US011453161B2

(12) United States Patent
Haidet et al.

(10) Patent No.: US 11,453,161 B2
(45) Date of Patent: Sep. 27, 2022

(54) PROCESSES FOR PRODUCING CURED POLYMERIC PRODUCTS BY ADDITIVE MANUFACTURING

(71) Applicant: Bridgestone Americas Tire Operations, LLC, Nashville, TN (US)

(72) Inventors: Andrew V. Haidet, Silver Lake, OH (US); Joshua P. Abell, Franklin, TN (US); Kung-Ching Liao, Copley, OH (US)

(73) Assignee: Bridgestone Americas Tire Operations, LLC, Nashville, TN (US)

( * ) Notice: Subject to any disclaimer, the term of this patent is extended or adjusted under 35 U.S.C. 154(b) by 781 days.

(21) Appl. No.: 16/342,575

(22) PCT Filed: Oct. 24, 2017

(86) PCT No.: PCT/US2017/057990
§ 371 (c)(1),
(2) Date: Apr. 17, 2019

(87) PCT Pub. No.: WO2018/081053
PCT Pub. Date: May 3, 2018

(65) Prior Publication Data
US 2020/0055237 A1 Feb. 20, 2020

Related U.S. Application Data

(60) Provisional application No. 62/413,459, filed on Oct. 27, 2016.

(51) Int. Cl.
| | |
|---|---|
| *B29C 64/165* | (2017.01) |
| *B29D 22/02* | (2006.01) |
| *B29D 30/08* | (2006.01) |
| *B29C 71/02* | (2006.01) |
| *C08J 7/18* | (2006.01) |
| *C08K 3/04* | (2006.01) |
| *C08K 3/06* | (2006.01) |
| *C08K 3/22* | (2006.01) |
| *C08K 5/00* | (2006.01) |
| *C08K 5/09* | (2006.01) |
| *C08L 19/00* | (2006.01) |
| *C08L 57/00* | (2006.01) |
| *C08L 87/00* | (2006.01) |
| *B33Y 70/00* | (2020.01) |
| *B33Y 80/00* | (2015.01) |

(52) U.S. Cl.
CPC .......... *B29C 64/165* (2017.08); *B29D 22/023* (2013.01); *B29D 30/08* (2013.01); *C08J 7/08* (2013.01); *C08J 7/18* (2013.01); *C08K 3/04* (2013.01); *C08K 3/06* (2013.01); *C08K 3/22* (2013.01); *C08K 5/0025* (2013.01); *C08K 5/09* (2013.01); *C08L 19/006* (2013.01); *C08L 57/00* (2013.01); *C08L 87/00* (2013.01); *B33Y 70/00* (2014.12); *B33Y 80/00* (2014.12); *C08K 2003/2296* (2013.01)

(58) Field of Classification Search
CPC ....... B29C 64/165; B33Y 70/00; B33Y 10/00; B33Y 30/00; B29D 22/023; B29D 30/08; C08J 7/08; C08J 7/17; C08K 3/04; C08K 3/06; C08K 3/22; C08K 5/0025; C08K 5/09; C08I 19/006; C08I 57/00; C08I 87/00

See application file for complete search history.

(56) References Cited

U.S. PATENT DOCUMENTS

| | | |
|---|---|---|
| 5,059,266 A | 10/1991 | Yamane et al. |
| 5,352,310 A | 10/1994 | Natter |
| 5,639,413 A | 6/1997 | Crivello |
| 5,738,817 A | 4/1998 | Danforth et al. |
| 5,952,152 A | 9/1999 | Cunningham et al. |
| 5,981,616 A | 11/1999 | Yamamura et al. |
| 5,985,510 A | 11/1999 | Akutsu et al. |
| 6,011,180 A | 1/2000 | Cunningham et al. |
| 6,013,714 A | 1/2000 | Haruta et al. |
| 6,022,906 A | 2/2000 | Ohwa et al. |
| 6,096,794 A | 8/2000 | Cunningham et al. |
| 6,130,025 A | 10/2000 | Chikaoka et al. |
| 6,243,616 B1 | 6/2001 | Droscher et al. |
| 6,281,307 B1 | 8/2001 | Muhlebach et al. |

(Continued)

FOREIGN PATENT DOCUMENTS

| | | |
|---|---|---|
| CA | 2810963 A1 | 9/2014 |
| CA | 2814605 A1 | 10/2014 |

(Continued)

OTHER PUBLICATIONS

"Elongation at Break or Fracture Strain: Technical Properties of Plastics," by Omnexus, copyright 2020, downloaded Nov. 24, 2020 from https://omnexus.specialchem.com/polymer-properties/properties/elongation-at-break (12 pages).

(Continued)

*Primary Examiner* — Mary Lynn F Theisen
(74) *Attorney, Agent, or Firm* — Shaun J. Fox

(57) ABSTRACT

Disclosed herein are processes for production of a cured polymeric product which processes include using rubber particles to form a rubber layer, applying liquid binder to form a bound layer from the rubber layer, and curing, whereby repetition of steps allows for formation of additional layers and ultimately production of the cured polymeric product.

24 Claims, No Drawings

(56) References Cited

U.S. PATENT DOCUMENTS

| | | |
|---|---|---|
| 6,323,295 B1 | 11/2001 | Muhlebach et al. |
| 6,332,943 B1 | 12/2001 | Herrmann et al. |
| 6,353,771 B1 | 3/2002 | Southland |
| 6,375,874 B1 | 4/2002 | Russell et al. |
| 6,379,796 B1 | 4/2002 | Uenishi et al. |
| 6,576,684 B1 | 6/2003 | Desobry et al. |
| 6,799,959 B1 | 10/2004 | Tochimoto et al. |
| 6,896,839 B2 | 5/2005 | Kubo et al. |
| 6,942,830 B2 | 9/2005 | Mulhaupt et al. |
| 7,105,206 B1 | 9/2006 | Beck et al. |
| 7,192,688 B2 | 3/2007 | Klang et al. |
| 7,232,498 B2 | 6/2007 | Zimmer et al. |
| 7,300,613 B2 | 11/2007 | Sano et al. |
| 7,307,123 B2 | 12/2007 | Johnson et al. |
| 7,381,360 B2 | 6/2008 | Oriakhi et al. |
| 7,381,516 B2 | 6/2008 | Arney et al. |
| 7,427,317 B2 | 9/2008 | Sloan |
| 7,455,804 B2 | 11/2008 | Patel et al. |
| 7,569,273 B2 | 8/2009 | Bredt et al. |
| 7,578,958 B2 | 8/2009 | Patel et al. |
| 7,641,752 B2 | 1/2010 | Nicolas et al. |
| 7,662,224 B2 | 2/2010 | Sloan |
| 7,744,803 B2 | 6/2010 | Jackson et al. |
| 7,795,349 B2 | 9/2010 | Bredt et al. |
| 7,923,121 B2 | 4/2011 | Jackson et al. |
| 8,157,908 B2 | 4/2012 | Williams |
| 8,362,148 B2 | 1/2013 | Messe et al. |
| 8,460,451 B2 | 6/2013 | Xu et al. |
| 8,603,612 B2 | 12/2013 | Chopra et al. |
| 8,653,153 B1 | 2/2014 | Vanbesien et al. |
| 8,801,986 B2 | 8/2014 | Matsui et al. |
| 8,822,590 B2 | 9/2014 | Hermes et al. |
| 8,876,513 B2 | 11/2014 | Lim et al. |
| 8,916,084 B2 | 12/2014 | Chretien et al. |
| 8,980,406 B2 | 3/2015 | Xu |
| 9,004,663 B2 | 4/2015 | Van Thillo et al. |
| 9,012,527 B2 | 4/2015 | Chopra et al. |
| 9,017,589 B2 | 4/2015 | Kritchman et al. |
| 9,023,566 B2 | 5/2015 | Martin |
| 9,029,058 B2 | 5/2015 | Martin |
| 9,098,000 B2 | 8/2015 | Hirth et al. |
| 9,403,323 B2 | 8/2016 | Seeler et al. |
| 10,683,381 B2 | 6/2020 | Abell et al. |
| 2001/0048182 A1 | 12/2001 | Caretta et al. |
| 2001/0050031 A1 | 12/2001 | Bredt et al. |
| 2002/0018959 A1 | 2/2002 | Lawton et al. |
| 2002/0048717 A1 | 4/2002 | Yamamura et al. |
| 2003/0054158 A1 | 3/2003 | Smith et al. |
| 2003/0059708 A1 | 3/2003 | Yamamura et al. |
| 2003/0090034 A1 | 5/2003 | Mulhaupt et al. |
| 2003/0162665 A1 | 8/2003 | Rokhvarger et al. |
| 2003/0198824 A1 | 10/2003 | Fong et al. |
| 2003/0224313 A1 | 12/2003 | Bergersen |
| 2003/0224314 A1 | 12/2003 | Bergersen |
| 2004/0020614 A1 | 2/2004 | Lindsay et al. |
| 2004/0023145 A1 | 2/2004 | Moussa et al. |
| 2004/0036200 A1 | 2/2004 | Patel et al. |
| 2004/0146806 A1 | 7/2004 | Roberts et al. |
| 2004/0171742 A1 | 9/2004 | Estrin |
| 2004/0259023 A1 | 12/2004 | Campagnola et al. |
| 2005/0014005 A1 | 1/2005 | Kramer et al. |
| 2005/0054798 A1 | 3/2005 | Klang et al. |
| 2005/0064333 A1 | 3/2005 | Crivello |
| 2005/0154121 A1 | 7/2005 | Fan et al. |
| 2005/0158660 A1 | 7/2005 | Lawton et al. |
| 2005/0220983 A1 | 10/2005 | Hayes |
| 2005/0280185 A1 | 12/2005 | Russell et al. |
| 2006/0008777 A1 | 1/2006 | Peterson et al. |
| 2006/0032569 A1 | 2/2006 | Zimmer et al. |
| 2006/0113714 A1 | 6/2006 | Giloh et al. |
| 2006/0141276 A1 | 6/2006 | Ito et al. |
| 2006/0154195 A1 | 7/2006 | Mather et al. |
| 2006/0155376 A1 | 7/2006 | Asgari |
| 2006/0159869 A1 | 7/2006 | Kramer et al. |
| 2006/0163774 A1 | 7/2006 | Abels et al. |
| 2006/0167147 A1 | 7/2006 | Asgari |
| 2006/0184005 A1 | 8/2006 | Sakezles |
| 2006/0208388 A1 | 9/2006 | Bredt et al. |
| 2006/0211802 A1 | 9/2006 | Asgari |
| 2006/0231982 A1 | 10/2006 | You |
| 2006/0247360 A1 | 11/2006 | Halasa et al. |
| 2006/0257511 A1 | 11/2006 | Iwamoto et al. |
| 2006/0290032 A1 | 12/2006 | Sano |
| 2007/0003749 A1 | 1/2007 | Asgari |
| 2007/0003753 A1 | 1/2007 | Asgari |
| 2007/0007698 A1 | 1/2007 | Sano |
| 2007/0043138 A1 | 2/2007 | Yamamura et al. |
| 2007/0049652 A1 | 3/2007 | Ito et al. |
| 2007/0060682 A1 | 3/2007 | Ito et al. |
| 2007/0072287 A1 | 3/2007 | Morisette et al. |
| 2007/0134596 A1 | 6/2007 | Lungu |
| 2007/0187117 A1 | 8/2007 | Tanaka et al. |
| 2007/0205528 A1 | 9/2007 | Patel et al. |
| 2007/0225458 A1 | 9/2007 | Kimura et al. |
| 2007/0232713 A1 | 10/2007 | Takase et al. |
| 2007/0241482 A1 | 10/2007 | Giller et al. |
| 2007/0245956 A1 | 10/2007 | Ruuttu et al. |
| 2007/0267884 A1 | 11/2007 | Failla et al. |
| 2008/0003372 A1 | 1/2008 | Kamps et al. |
| 2008/0021126 A1 | 1/2008 | Dietliker et al. |
| 2008/0057101 A1 | 3/2008 | Roorda |
| 2008/0075668 A1 | 3/2008 | Goldstein |
| 2008/0135502 A1 | 6/2008 | Pyo et al. |
| 2008/0236597 A1 | 10/2008 | Bergersen |
| 2008/0241404 A1 | 10/2008 | Sandrine et al. |
| 2008/0258345 A1 | 10/2008 | Bens et al. |
| 2009/0101278 A1 | 4/2009 | Laberge-Lebel et al. |
| 2009/0148813 A1 | 6/2009 | Sun et al. |
| 2009/0176034 A1 | 7/2009 | Ruuttu et al. |
| 2009/0287332 A1 | 11/2009 | Adusumilli et al. |
| 2010/0015408 A1 | 1/2010 | Fong et al. |
| 2010/0053287 A1 | 3/2010 | Belelie et al. |
| 2010/0055484 A1 | 3/2010 | Chretien et al. |
| 2010/0104832 A1 | 4/2010 | Messe et al. |
| 2010/0119835 A1 | 5/2010 | Messe et al. |
| 2010/0140850 A1 | 6/2010 | Napadensky et al. |
| 2010/0181706 A1 | 7/2010 | Ruuttu et al. |
| 2010/0196624 A1 | 8/2010 | Ruuttu et al. |
| 2010/0227941 A1 | 9/2010 | Ueda et al. |
| 2010/0230850 A1 | 9/2010 | Sanderson |
| 2010/0279007 A1 | 11/2010 | Briselden et al. |
| 2010/0304088 A1 | 12/2010 | Steeman et al. |
| 2011/0059291 A1 | 3/2011 | Boyce et al. |
| 2011/0200655 A1 | 8/2011 | Black et al. |
| 2011/0262711 A1 | 10/2011 | Chopra et al. |
| 2011/0293522 A1 | 12/2011 | Wang et al. |
| 2011/0293891 A1 | 12/2011 | Leyden et al. |
| 2011/0304082 A1 | 12/2011 | Dusseaux et al. |
| 2011/0309556 A1 | 12/2011 | Lauwers |
| 2011/0309728 A1 | 12/2011 | Diebel |
| 2011/0318532 A1 | 12/2011 | Dusseaux et al. |
| 2011/0319745 A1 | 12/2011 | Frey |
| 2012/0048439 A1 | 3/2012 | Christenbury |
| 2012/0055601 A1 | 3/2012 | Christenbury |
| 2012/0060468 A1 | 3/2012 | Dushku et al. |
| 2012/0168049 A1 | 7/2012 | Jenkins et al. |
| 2012/0174661 A1 | 7/2012 | Hergenrother et al. |
| 2012/0260492 A1 | 10/2012 | Bonnet et al. |
| 2012/0289657 A1 | 11/2012 | Hilf et al. |
| 2012/0309895 A1 | 12/2012 | Schmidt et al. |
| 2013/0002773 A1 | 1/2013 | Fujii et al. |
| 2013/0026683 A1 | 1/2013 | Ng et al. |
| 2013/0031888 A1 | 2/2013 | Fuller |
| 2013/0053995 A1 | 2/2013 | Hashimoto et al. |
| 2013/0079877 A1 | 3/2013 | Buma et al. |
| 2013/0083276 A1 | 4/2013 | Iwahashi et al. |
| 2013/0090407 A1 | 4/2013 | Carter et al. |
| 2013/0149182 A1 | 6/2013 | Sreshta et al. |
| 2013/0164401 A1 | 6/2013 | Dusseaux |
| 2013/0165586 A1 | 6/2013 | Hashimoto |
| 2013/0170171 A1 | 7/2013 | Wicker et al. |
| 2013/0171431 A1 | 7/2013 | Swartz et al. |
| 2013/0172480 A1 | 7/2013 | Schmidt et al. |
| 2013/0206291 A1 | 8/2013 | Emorine et al. |

(56) References Cited

U.S. PATENT DOCUMENTS

| | | | |
|---|---|---|---|
| 2013/0213543 | A1 | 8/2013 | Christenbury et al. |
| 2013/0225779 | A1 | 8/2013 | Ruggieri et al. |
| 2013/0227901 | A1 | 9/2013 | Zohar |
| 2013/0241114 | A1 | 9/2013 | Ravich et al. |
| 2013/0288062 | A1 | 10/2013 | van Loon et al. |
| 2013/0292117 | A1 | 11/2013 | Robisson et al. |
| 2013/0297062 | A1 | 11/2013 | Lacaze et al. |
| 2013/0303678 | A1 | 11/2013 | Hilf et al. |
| 2013/0310484 | A1 | 11/2013 | Furukawa |
| 2013/0317164 | A1 | 11/2013 | Hermes et al. |
| 2013/0320467 | A1 | 12/2013 | Buchanan et al. |
| 2013/0335807 | A1 | 12/2013 | Arsenault et al. |
| 2013/0344232 | A1 | 12/2013 | Chopra et al. |
| 2014/0017460 | A1 | 1/2014 | Xu et al. |
| 2014/0061974 | A1 | 3/2014 | Tyler |
| 2014/0067106 | A1 | 3/2014 | Makeig |
| 2014/0072712 | A1 | 3/2014 | Xu |
| 2014/0075810 | A1 | 3/2014 | Mikroulis |
| 2014/0081192 | A1 | 3/2014 | Wenske et al. |
| 2014/0110872 | A1 | 4/2014 | Levy et al. |
| 2014/0121327 | A1 | 5/2014 | Schmidt et al. |
| 2014/0131908 | A1 | 5/2014 | Sun et al. |
| 2014/0147538 | A1 | 5/2014 | Bonnet |
| 2014/0162033 | A1 | 6/2014 | Giller |
| 2014/0249406 | A1 | 9/2014 | Flynn et al. |
| 2014/0259325 | A1 | 9/2014 | Behrend et al. |
| 2014/0259327 | A1 | 9/2014 | Demarest |
| 2014/0265033 | A1 | 9/2014 | Woloszyn et al. |
| 2014/0265034 | A1 | 9/2014 | Dudley |
| 2014/0268607 | A1 | 9/2014 | Wicker et al. |
| 2014/0271328 | A1 | 9/2014 | Burris et al. |
| 2014/0284832 | A1 | 9/2014 | Novikov et al. |
| 2014/0323967 | A1 | 10/2014 | Mancino |
| 2014/0339741 | A1 | 11/2014 | Aghababaie et al. |
| 2014/0339745 | A1 | 11/2014 | Uram |
| 2014/0348692 | A1 | 11/2014 | Bessac et al. |
| 2014/0353862 | A1 | 12/2014 | Erdman |
| 2015/0024169 | A1 | 1/2015 | Martin |
| 2015/0032241 | A1 | 1/2015 | Lee et al. |
| 2015/0079362 | A1 | 3/2015 | Yang et al. |
| 2015/0102532 | A1 | 4/2015 | DeSimone et al. |
| 2015/0137426 | A1 | 5/2015 | Van Esbroeck et al. |
| 2015/0153282 | A1 | 6/2015 | Eastman |
| 2015/0268099 | A1 | 9/2015 | Craig et al. |
| 2016/0271872 | A1 | 9/2016 | Sand |
| 2017/0369620 | A1 | 12/2017 | Abell et al. |
| 2017/0371350 | A1 | 12/2017 | Engdahl et al. |
| 2018/0370123 | A1 | 12/2018 | Abell et al. |
| 2019/0248067 | A1* | 8/2019 | Achten ................ B29C 64/165 |

FOREIGN PATENT DOCUMENTS

| | | | |
|---|---|---|---|
| CN | 1566244 | A | 1/2005 |
| CN | 1688938 | A | 10/2005 |
| CN | 1290953 | C | 12/2006 |
| CN | 101495561 | A | 7/2009 |
| CN | 102660107 | A | 9/2012 |
| CN | 103232608 | A | 8/2013 |
| CN | 103707507 | A | 4/2014 |
| CN | 103980592 | A | 8/2014 |
| CN | 103992560 | A | 8/2014 |
| CN | 203844238 | U | 9/2014 |
| CN | 104149371 | A | 11/2014 |
| DE | 10143218 | A1 | 8/2002 |
| DE | 102004028462 | A1 | 12/2005 |
| DE | 102012102322 | A1 | 9/2013 |
| DE | 102012211450 | A1 | 1/2014 |
| EP | 1652644 | A1 | 5/2006 |
| EP | 1757667 | A2 | 2/2007 |
| EP | 1757979 | A1 | 2/2007 |
| EP | 1967284 | A2 | 9/2008 |
| EP | 2030762 | A1 | 3/2009 |
| EP | 2399695 | A1 | 12/2011 |
| EP | 2540783 | A1 | 1/2013 |
| EP | 1960986 | B1 | 5/2013 |
| EP | 2671759 | A1 | 12/2013 |
| JP | 2004051665 | A | 2/2004 |
| JP | 2006002110 | A | 1/2006 |
| JP | 2007137957 | A | 6/2007 |
| JP | 2010-512255 | A | 4/2010 |
| JP | 2010094893 | A | 4/2010 |
| JP | 2012074644 | A | 4/2012 |
| JP | 2013-540627 | A | 11/2013 |
| JP | 2014-503384 | A | 2/2014 |
| JP | 2014034270 | A | 2/2014 |
| JP | 2014-083744 | A | 5/2014 |
| JP | 2014-0136311 | A | 7/2014 |
| JP | 2015-506855 | A | 3/2015 |
| WO | 0053398 | A1 | 9/2000 |
| WO | 0059972 | A1 | 10/2000 |
| WO | 0157094 | A2 | 8/2001 |
| WO | 2006102238 | A2 | 9/2006 |
| WO | 2007006850 | A2 | 1/2007 |
| WO | 2008113813 | A1 | 9/2008 |
| WO | 2010061235 | A1 | 6/2010 |
| WO | 2010072961 | A2 | 7/2010 |
| WO | 2012171055 | A1 | 12/2012 |
| WO | 2013013566 | A1 | 1/2013 |
| WO | 2013086577 | A1 | 6/2013 |
| WO | 2013090885 | A2 | 6/2013 |
| WO | 2013092994 | A1 | 6/2013 |
| WO | 2013127655 | A1 | 9/2013 |
| WO | 2013128452 | A1 | 9/2013 |
| WO | 2013146527 | A1 | 10/2013 |
| WO | 2013164599 | A1 | 11/2013 |
| WO | 2014060450 | A1 | 4/2014 |
| WO | 2014077848 | A1 | 5/2014 |
| WO | 2014090492 | A1 | 6/2014 |
| WO | 2014179568 | A2 | 11/2014 |
| WO | 2014204450 | A1 | 12/2014 |
| WO | 2014204476 | A1 | 12/2014 |
| WO | 2014209994 | A2 | 12/2014 |
| WO | 2014210584 | A1 | 12/2014 |
| WO | 2015118552 | A1 | 8/2015 |
| WO | 2015-148613 | A1 | 10/2015 |
| WO | 2015176141 | A1 | 11/2015 |
| WO | 2016067584 | A1 | 5/2016 |
| WO | 2016-106062 | A1 | 6/2016 |

OTHER PUBLICATIONS

Material Data Book from Cambridge University Engineering Department, 2003 Edition (41 pages).
Written Opinion from PCT application PCT/US2017/057990 dated Feb. 2018.
International Search Report from PCT application PCT/US2017/057990 dated Feb. 2018.
Extended European Search Report and Search Opinion from EP application 17865318.4 dated May 20, 2019.
Extended European Search Report from EP application 16876406.6 dated Aug. 13, 2019.
International Search Report and Written Opinion from PCT application No. PCT/US2015/066288 (13 pages), dated Apr. 2016.
International Search Report and Written Opinion from PCT application No. PCT/US2016/065360 (15 pages), dated Feb. 2017.
Aliakbari, Mina, "Additive Manufacturing: State-of-th-Art, Capabilities, and Sample Applications with Cost Analysis," Master of Science Thesis, Production Engineering and Management, Department of Industrial Production, pp. 1-90 (Jun. 2012).
Arceneaux, Jo Ann et al., "UV & EB Chemistry and Technology," RadTech Printer's Guide, pp. 1-8 (undated, printed Oct. 2018).
Abstract of Baldeck, P. L. et al., "Laser-induced binding of precured rubber compounds," Optical Engineering, vol. 30, No. 3, pp. 312-316 (Mar. 1991).
Abstract of Decker, Christian, "Kinetic Study and New Applications of UV Radiation Curing," Macromolecular Rapid Communications, vol. 23, Issue 18, pp. 1067-1093, doi: 10.1002/marc.200290014 (2002).
Duan, Yugang et al., "Effects of compaction and UV exposure on performance of acrylate/glass-fiber composites cured layer by layer,"

(56) References Cited

OTHER PUBLICATIONS

Journal of Applied Polymer Science, vol. 123, Issue 6, pp. 3799-3805, doi: 10.1002/app.34909 (Mar. 15, 2012).
Duann, "Introducing 3D Printed Black Elasto Plastic: I Can't Believe It's Not Rubber," Shapeways Magazine, 3D Printing News and Innovation, 12 pp., downloaded from https://www.shapeways.com/blog/archives/1375-introducing-3d-printed-black-elasto-plastic-i-cant-believe-its-not-rubber.html (May 17, 2012).
Eggers, Karin, Interational Search Report with Written Opinion from PCT Application No. PCT/US2015/066288, 13 pp. (Apr. 4, 2016).
Abstract of Elsner, C. et al., "3D-Microstructure Replication Processes Using UV-Curable Acrylates," Microelectronic Engineering, vol. 65, Issues 1-2, pp. 163-170 (Jan. 2003).
Esquivel de la Garza, Alejandro et al., "UV Curing with Lasers," Adhesives Magazine, downloaded from http://www.adhesivesmag.com/articles/print/91983-uv-curing-with-lasers on Nov. 19, 2014, 6 pp.
Ganter, B. et al., "UV-Curing Silicone Rubbers find uses in new of application fields," Rubber Fibres Plastics International Magazine for the Polymer Industry, Special Reprint, pp. 1-4 (2013).
Abstract of Guo, Qiuquan et al., "'Paintable' 3D printed structures via a post-ATRP process with antimicrobial function for biomedical applications," Journal of Materials Chemistry B, vol. 1, No. 48, pp. 6644-6649 (Dec. 28, 2013).
Herderick, E., "Additive Manufacturing of Metals: A Review," Materials Science and Technology, pp. 1413-1425 (2011).
Presentation by Stephen Heston and Stan K. Kulikowski entitled: "Flexing the 3D Imagination: The genesis of NinjaFlex™ 3D flexible filament for desktop printing," pp. 1-7 (Apr. 25, 2014).
Jirman, R. et al., "Individual Replacement of the Frontal Bone Defect: Case Report," Prague Medical Report, vol. 110, No. 1, pp. 79-84 (2009).
Kaelin, Brooke, "Chinese Researchers Invent Regenovo Bioprinter," 2 pp. (Aug. 11, 2013).
Kolczak, Urszula et al., "Reaction Mechanism of Monoacyl- and Bisacylphosphine Oxide Photoinitiators Studied by 31P-, 13C-, and 1H-CIDNP and ESR," Journal of American Chemical Society, vol. 118, pp. 6477-6489 (1996).
Lee, Myung Jin, International Search Report with Written Opinion from PCT Application No. PCT/US2016/065360, 15 pp. (Feb. 20, 2017).
Abstract of Meniga, Tarle Z. et al., "Polymerization of composites using pulsed laser," European Journal of Oral Sciences, vol. 103, pp. 394-398 (1995).
Abstract of Sun, X. et al., "Intermittent curing and its effect on pulsed laser-induced photopolymerization," Applied Physics B, vol. 92, Issue 1, pp. 93-98 (printed on Nov. 19, 2014).
Abstract of Suri, Shalu et al., "Solid freeform fabrication of designer scaffolds of hyaluronic acid for nerve tissue engineering," Biomedical Microdevices, vol. 13, Issue 6, pp. 983-993 (Dec. 2011).
Tehfe, Mohamad-Ali et al., "Polyaromatic Structures as Organo-Photoinitiator Catalysts for Efficient Visible Light Induced Dual Radical/Cationic Photopolymerization and Interpenetrated Polymer Networks Synthesis," Macromolecules, vol. 45, pp. 4454-4460 (2012).
Abstract of Tillier, Delphine L. et al., "About crosslinking of low molecular weight ethylene-propylene(-diene) copolymer-based artificial latices," Journal of Polymer Science Part A: Polymer Chemistry, vol. 43, Issue 16, pp. 3600-3615, doi: 10.1002/pola.20807 (Aug. 15, 2005).
Abstract of Umezu, Shinjiro et al., "Fundamental Characteristics of Bioprint on Calcium Alginate Gel," Japanese Journal of Applied Physics, vol. 52, No. 5S1, 2 pp. (May 20, 2013).

Yang, H. et al., "High Viscosity Jetting System for 3D Reactive Inkjet Printing," 24th Annual International Solid Freeform Fabrication Symposium, An Additive Manufacturing Conference, pp. 505-513 (Jan. 2013).
Abstract of Wang, Xiaolong et al., "I3DP, a robust 3D printing approach enabling genetic post-printing surface modification," Chemical Communications, vol. 49, No. 86, pp. 10064-10066 (Nov. 7, 2013).
Abstract of Williams, Richard R. et al., "Composite Sandwich Structures With Rapid Prototyped Cores," Rapid Prototyping Journal, vol. 17, No. 2, pp. 92-97 (2011).
Abstract of Xu, Renmei et al., "Flexographic Platemaking Using Rapid Prototyping Technologies," Proceedings of the Technical Association of the Graphic Arts, TAGA, pp. 1-11 (2008).
Zhang, Jing et al., "Structure design of naphthalimide derivatives: Toward versatile photoinitiators for Near-UV/Visible LEDs, 3D printing, and water-soluble photoinitiating systems," Macromolecules, vol. 48, No. 7, pp. 2054-2063 (Apr. 14, 2015).
3D Systems Corporation, "3D System's ProJet 660 the Ultimate Solution for Hankook Tire Concept Design," 2 pp. (2014).
3D Systems, Inc., "Continental Tire Cruises Through Tire Design With 3D Systems 3D Printing Solution," 2 pp. (Jan. 2012).
3D Systems, Inc., "DuraForm Flex (SLS)," downloaded from http://www.3dsystems.com/materials/duraformr-flex in Oct. 2018, 4 pp.
Fenner Drives, NinjaFlex® Flexible 3D Printing Filament by NinjaTek®, 3 pp., downloaded from http://www.fennerdrives.com/product-lines/_/3d/?= on Sep. 17, 2018.
Formerol F.10/Sugru Technical Data Sheet v 2.3, pp. 1-12 (Sep. 2016).
Hyrel 3D printout from website, 5 pp. (undated, printed Oct. 2018).
Maker Geeks 3D Printing Filament Blog, Flex EcoPLA-Flexible 3D Printer Filament, 17 pp., downloaded from http://makergeeks.blogspot.com/2013/05/flex-ecopla-flexible-3d-printer.html in Oct. 2018.
Mataerial, "A radically new 3D printing method," 7 pp., downloaded from http://www.mataerial.com on Oct. 4, 2018.
A look inside Materialise, the Belgian company 3D printing its way into the future of everything, 16 pp. (printed Oct. 4, 2018).
Materials Science; Studies from University of Western Ontario Yield New Data on Materials Science, Technology & Business Journal, 1404 (Apr. 22, 2014), Publisher: NewsRx, ISSN 1945-8398, ProQuest Document ID: 1516993358.
Object, "FullCure Materials," 4 pp. (2008.).
Palmiga Innovation, "Rubber 3D printing—Makerbot Replicator 3DP Rubber Fliament Mod," 10 pp., downloaded from http://palmiga.com/design-2/design/makerbot-replicator-rubber-fdm-mod/ (undated, printed Oct. 2018).
PL Industries, LLC Brochure, 1 pg. (Mar. 2012).
Regenovo 3D Bioprinter, 7 pp. (undated, printed Oct. 2018).
Stratasys, PolyJet Materials Data Sheet, 3 pp. (2014).
Stratasys, TangoPlus Polyjet Material Specifications, 1 pg. (2014).
Structur3D Printing, "Introducing the Discov3ry 2.0: A Fully Integrated 3D Printer System for Two Part Materials," 4 pp., downloaded from http://www.structur3d.io/#discov3ry (undated, printed Oct. 2018).
TNO Science and Industry, "High-viscous material inkjet printer: Inkjet as manufacturing process," 2 pp., downloaded from https://www.tno.nl/downloads/tno_highviscous_material_inkjetprinted.pdf (undated, printed Oct. 2018).
Kai, Du, et al., "Progress on Research Application of High Trans-butadiene-iosprene Copolymer (TBIR) Rubber," Special Purpose Rubber Products, vol. 25, No. 6, Dec. 2004, pp. 54-58.

* cited by examiner

PROCESSES FOR PRODUCING CURED POLYMERIC PRODUCTS BY ADDITIVE MANUFACTURING

FIELD

The present application is directed to production of a cured polymeric product by a process that includes using rubber particles to form a rubber layer, applying liquid binder to form a bound layer from the rubber layer, and curing, whereby repetition of steps allows for formation of additional layers and ultimately production of the cured polymeric product.

BACKGROUND

Additive manufacturing (which encompasses processes such as "3D Printing") is a process whereby a three-dimensional article is manufactured (such as by printing) layer by layer from raw material. Certain additive manufacturing processes manufacture an article by building up cross-sectional layers of the article as compared to other so-called subtractive manufacturing processes which require that certain portions of a manufactured article be removed in order to produce the article in its final shape or form. While various additive manufacturing methods have existed since the 1980s, certain of them have been focused upon the use of various plastic polymers such as acrylonitrile butadiene styrene (ABS), polycarbonate (PC), high density polyethylene (HDPE), and high impact polystyrene (HIPS).

SUMMARY

Disclosed herein are processes for production of a cured polymeric product which processes include using rubber particles to form a rubber layer, applying liquid binder to form a bound layer from the rubber layer, and curing, whereby repetition of steps allows for formation of additional layers and ultimately production of the cured polymeric product.

In a first embodiment, a process is disclosed for producing a cured polymeric product, preferably a tire component or an air spring, by additive manufacturing. The process comprises: providing an additive manufacturing device comprising a source of actinic radiation, a tank capable of containing a binder, and a support structure; forming rubber particles into a first rubber layer upon the support structure, wherein the rubber particles comprise at least one conjugated diene-monomer containing polymer and reinforcing filler, preferably carbon black, silica, or a combination thereof; applying liquid binder to the first rubber layer to form a first bound layer, wherein the liquid binder comprises a curable polymeric mixture and optionally a cure package; sequentially forming additional rubber layers upon the first bound layer and applying liquid binder to at least some of the additional rubber layers to form additional bound layers; and effecting curing by applying actinic radiation, heat, or a combination thereof to one or more of the bound layers, thereby producing a cured polymeric product.

In a second embodiment, a process is disclosed for producing a cured polymeric product, preferably a tire component or an air spring, by additive manufacturing. The process comprises: providing an additive manufacturing device comprising a source of actinic radiation, a tank capable of containing a binder, and a support structure; forming rubber particles into a first rubber layer upon the support structure, wherein the rubber particles comprise at least one uncured conjugated diene-monomer containing polymer and reinforcing filler, preferably carbon black, silica, or a combination thereof; applying liquid binder to the first rubber layer upon the substrate surface to form a first bound layer, wherein the liquid binder comprises a curable polymeric mixture and optionally a cure package; sequentially forming additional rubber layers upon the first bound layer and applying liquid binder to at least some of the additional rubber layers to form additional bound layers; effecting curing by applying actinic radiation, heat, or a combination thereof to one or more of the bound layers, thereby producing a cured polymeric product.

In a third embodiment, a process is disclosed for producing a cured polymeric product, preferably a tire component or an air spring, by additive manufacturing. The process comprises: providing an additive manufacturing device comprising a source of actinic radiation, a tank capable of containing a binder, and a support structure; forming rubber particles into a first rubber layer upon the support structure, wherein the rubber particles comprise at least one cured conjugated diene-monomer containing polymer and reinforcing filler, preferably carbon black, silica, or a combination thereof; applying liquid binder to the first rubber layer upon the substrate surface to form a first bound layer, wherein the liquid binder comprises a curable polymeric mixture and optionally a cure package; sequentially forming additional rubber layers upon the first bound layer and applying liquid binder to at least some of the additional rubber layers to form additional bound layers; effecting curing by applying actinic radiation, heat, or a combination thereof to one or more of the bound layers, thereby producing a cured polymeric product.

In a fourth embodiment, a process is disclosed for producing a cured polymeric product, preferably a tire component or an air spring, by additive manufacturing. The process comprises: providing an additive manufacturing device comprising a source of actinic radiation, a tank capable of containing a binder, and a support structure; forming rubber particles into a first rubber layer upon the support structure, wherein the rubber particles comprise at least one conjugated diene-monomer containing polymer and reinforcing filler, preferably carbon black, silica, or a combination thereof; applying liquid binder to the first rubber layer to form a first bound layer wherein the liquid binder comprises an actinic radiation curable polymeric mixture and optionally a cure package; sequentially forming additional rubber layers upon the first bound layer and applying liquid binder to at least some of the additional rubber layers to form additional bound layers; effecting curing by applying actinic radiation, heat, or a combination thereof to one or more of the bound layers, thereby producing a cured polymeric product. According to the fourth embodiment, the actinic radiation curable polymeric mixture of the liquid binder comprises: (i) a polyfunctionalized diene monomer-containing polymer having the formula: $[P][F]_n$ wherein P represents a diene monomer-containing polymer chain, F represents a functional group, n is 2 to about 15, and each F can be the same or different; (ii) optionally a chain extender based upon F or reactive with F; (iii) at least one actinic radiation sensitive photoinitiator; (iv) optionally a photosensitizer; and (v) a polyfunctional crosslinker reactive with F.

DETAILED DESCRIPTION

Disclosed herein are processes for production of a cured polymeric product which processes include using rubber particles to form a rubber layer, applying liquid binder to form a bound layer from the rubber layer, and curing, whereby repetition of steps allows for formation of additional layers and ultimately production of the cured polymeric product.

In a first embodiment, a process is disclosed for producing a cured polymeric product, preferably a tire component or an air spring, by additive manufacturing. The process comprises: providing an additive manufacturing device comprising a source of actinic radiation, a tank capable of containing a binder, and a support structure; forming rubber particles into a first rubber layer upon the support structure, wherein the rubber particles comprise at least one conjugated diene-monomer containing polymer and reinforcing filler, preferably carbon black, silica, or a combination thereof; applying liquid binder to the first rubber layer to form a first bound layer, wherein the liquid binder comprises a curable polymeric mixture and optionally a cure package; sequentially forming additional rubber layers upon the first bound layer and applying liquid binder to at least some of the additional rubber layers to form additional bound layers; and effecting curing by applying actinic radiation, heat, or a combination thereof to one or more of the bound layers, thereby producing a cured polymeric product.

In a second embodiment, a process is disclosed for producing a cured polymeric product, preferably a tire component or an air spring, by additive manufacturing. The process comprises: providing an additive manufacturing device comprising a source of actinic radiation, a tank capable of containing a binder, and a support structure; forming rubber particles into a first rubber layer upon the support structure, wherein the rubber particles comprise at least one uncured conjugated diene-monomer containing polymer and reinforcing filler, preferably carbon black, silica, or a combination thereof; applying liquid binder to the first rubber layer upon the substrate surface to form a first bound layer, wherein the liquid binder comprises a curable polymeric mixture and optionally a cure package; sequentially forming additional rubber layers upon the first bound layer and applying liquid binder to at least some of the additional rubber layers to form additional bound layers; effecting curing by applying actinic radiation, heat, or a combination thereof to one or more of the bound layers, thereby producing a cured polymeric product.

In a third embodiment, a process is disclosed for producing a cured polymeric product, preferably a tire component or an air spring, by additive manufacturing. The process comprises: providing an additive manufacturing device comprising a source of actinic radiation, a tank capable of containing a binder, and a support structure; forming rubber particles into a first rubber layer upon the support structure, wherein the rubber particles comprise at least one cured conjugated diene-monomer containing polymer and reinforcing filler, preferably carbon black, silica, or a combination thereof; applying liquid binder to the first rubber layer upon the substrate surface to form a first bound layer, wherein the liquid binder comprises a curable polymeric mixture and optionally a cure package; sequentially forming additional rubber layers upon the first bound layer and applying liquid binder to at least some of the additional rubber layers to form additional bound layers; effecting curing by applying actinic radiation, heat, or a combination thereof to one or more of the bound layers, thereby producing a cured polymeric product.

In a fourth embodiment, a process is disclosed for producing a cured polymeric product, preferably a tire component or an air spring, by additive manufacturing. The process comprises: providing an additive manufacturing device comprising a source of actinic radiation, a tank capable of containing a binder, and a support structure; forming rubber particles into a first rubber layer upon the support structure, wherein the rubber particles comprise at least one conjugated diene-monomer containing polymer and reinforcing filler, preferably carbon black, silica, or a combination thereof; applying liquid binder to the first rubber layer to form a first bound layer wherein the liquid binder comprises an actinic radiation curable polymeric mixture and optionally a cure package; sequentially forming additional rubber layers upon the first bound layer and applying liquid binder to at least some of the additional rubber layers to form additional bound layers; effecting curing by applying actinic radiation, heat, or a combination thereof to one or more of the bound layers, thereby producing a cured polymeric product. According to the fourth embodiment, the actinic radiation curable polymeric mixture of the liquid binder comprises: (i) a polyfunctionalized diene monomer-containing polymer having the formula: $[P][F]_n$ wherein P represents a diene monomer-containing polymer chain, F represents a functional group, n is 2 to about 15, and each F can be the same or different; (ii) optionally a chain extender based upon F or reactive with F; (iii) at least one actinic radiation sensitive photoinitiator; (iv) optionally a photosensitizer; and (v) a polyfunctional crosslinker reactive with F.

Definitions

The terminology as set forth herein is for description of the embodiments only and should not be construed as limiting the invention as a whole.

As used herein, the phrase "actinic radiation" refers to electromagnetic radiation capable of producing photochemical reactions. Actinic radiation includes, but is not limited to, UV, IR and microwave forms of radiation.

As used herein, the phrase "additive manufacturing" refers to the process of joining materials to make objects from 3D model data, usually layer upon layer, as opposed to subtractive manufacturing methodologies.

As used herein, the phrase "chain extender" refers to a monofunctionalized hydrocarbon or hydrocarbon derivative containing a functional group that reacts with a functional end group of a diene polymer chain and adds to the polymer chain, thereby increasing its molecular weight.

As used herein, the phrase "polyfunctional crosslinker" refers to a hydrocarbon or hydrocarbon derivative containing two or more functional groups which are capable of undergoing a reaction to provide cross-linking between two diene polymer chains or within a diene polymer chain.

As used herein, the term "hydrocarbon" refers to a compound consisting entirely of carbon and hydrogen atoms.

As used herein, the phrase "hydrocarbon derivative" refers to a hydrocarbon containing at least one heteroatom (e.g., N, O, S).

As used herein, the term "mer" or "mer unit" means that portion of a polymer derived from a single reactant molecule (e.g., ethylene mer has the general formula —CH2CH2-).

As used herein, the term "(meth)acrylate" encompasses both acrylate and methacrylate.

As used herein, the term "photoinitiator" refers to a compound that generates free radicals. The term "photoinitiator" is used interchangeably herein with the phrase "actinic radiation sensitive photoinitiator."

As used herein, the term "photosensitizer" refers to a light absorbing compound used to enhance the reaction of a photoinitiator. Upon photoexcitation, a photosensitizer leads to energy or electron transfer to a photoinitiator.

As used herein, the term "polyfunctionalized" refers to more than one functionalization and includes polymers that have been di-functionalized, tri-functionalized, etc. Generally, functionalization of a polymer may occur at one or both ends of a polymer chain, along the backbone of the polymer chain, in a side chain, and combinations thereof.

As used herein, the term "polymer" refers to the polymerization product of two or more monomers and is inclusive of homo-, co-, ter-, tetra-polymers, etc. Unless indicated to the contrary herein, the term polymer includes oligomers.

Cured Polymeric Products

As discussed above, the processes of the first-fourth embodiments are directed to producing a cured polymeric product. In certain preferred embodiments of the first-fourth embodiments, the cured polymeric product is a tire component or an air spring. Thus, disclosed herein, is a cured polymeric product produced according to the processes of the first, second, third, or fourth embodiments disclosed herein. In certain embodiments of the first-fourth embodiments, the cured polymeric product is a tire component. Exemplary such tire components include a tread, a bead, bead filler, belt wedge, a sidewall, an innerliner, an antenna tread, a cap ply or a cap layer, an undertread, a wing, an abrasion strip, a rim guard, and a subtread. In certain embodiments of the first-fourth embodiments, the cured polymeric product is an air spring. In certain embodiments of the first-fourth embodiments, the cured polymeric product is a product other than a tire component or an air spring; exemplary such products include durable goods, including, but not limited to belts, gaskets, seals, bushings, dampeners, handles, grips, and bumpers. In certain embodiments of the first-fourth embodiments, the cured polymeric product is a product other than a decorative product; in other words, in certain embodiments of the first-fourth embodiments, the cured polymeric product is a non-decorative product and has at least one function other than merely being decorative. The foregoing cured polymeric products resulting from the process of the first, second, third, or fourth embodiments (each in all of their variations as fully described throughout this application) should be considered to be fully disclosed herein. Also disclosed herein, is a tire comprising at least one tire component resulting from the process of the first, second, third, or fourth embodiments (each in all of their variations as fully described throughout this application).

Additive Manufacturing Device

As discussed above, according to the processes of the first-fourth embodiments, an additive manufacturing device is provided and utilized in the respective processes. The type of additive manufacturing device is not particularly limited as long as it is capable of completing the steps of the disclosed processes. Generally, additive manufacturing devices suitable for use in the processes of the first-fourth embodiments will comprise (include) a source of actinic radiation, a tank capable of containing a binder, and a support structure. According to the processes of the first-fourth embodiments, the tank of the additive manufacturing device is capable of containing the liquid binder; in certain embodiments of the first-fourth embodiments, the tank of the additive manufacturing device is refillable with liquid binder and in other embodiments the tank is replaceable (e.g., with a new container of liquid binder). In certain embodiments of the first-fourth embodiments, the additive manufacturing device includes at least one heater for heating the liquid binder prior to applying the liquid binder to the first rubber layer and additional rubber layers, for effecting curing of bound layers, or for a combination of both. According to the processes of the first-fourth embodiments, the support structure is used for forming of the rubber layers, i.e., the rubber particles are formed into rubber layers upon the surface of the support structure. According to certain embodiments of the first-fourth embodiments, the support structure has a flat upper surface so as to facilitate formation of the rubber layers upon its surface. Generally, according to the processes of the first-fourth embodiments, the support structure will be capable of vertical (i.e., up and down) movement so as to accommodate the layer-by-layer production of the cured polymeric product by the accumulation of additional rubber layers and bound layers. In certain embodiments of the first-fourth embodiments, the process comprises a tank and/or bed (capable of vertical or up and down movement) to accommodate the rubber particles. In such processes, each rubber layer that is formed is coated with liquid binder and then cured after which the bed or tank moves downward. Thereafter, additional rubber particles are spread over the surface of the previous bound and cured layer followed by binding and curing, with repetition until the desired number of bound and cured layers have been created.

In certain embodiments of the processes of the first-fourth embodiments, the additive manufacturing device cures the bound layers by a process that comprises solidifying each layer by using actinic radiation to provide at least one pattern on the surface of the bound layer, such a process can be referred to as laser rastering. In certain embodiments of the processes of the first-fourth embodiments, the laser rastering can be understood as involving the use of pinpoint radiation which is moved across the surface of the bound layer to result in an overall pattern being provided. In certain embodiments of the processes of the first-fourth embodiments, the additive manufacturing device forms the product by a process that comprises solidifying each layer by using actinic radiation to project at least one image on the liquid material, such a process can be referred to as digital light processing. As used herein, the phrase tracing a pattern in the liquid material is intended to encompass both digital light processing and laser rastering processes. In certain embodiments of the first-fourth embodiments, the liquid binder is applied (by additive manufacturing device) to the rubber layer(s) by dispensing the liquid binder from a printing head having a set of nozzles; in certain such embodiments, such a process can be referred to as material jetting.

According to the processes of the first-fourth embodiments, the materials of construction for the support structure of the additive manufacturing device upon which the layers of the cured polymeric product are formed may vary. In certain embodiments of the first-fourth embodiments, the support structure comprises polysiloxane polymer (e.g., polydimethylsiloxane or PDMS), a halogenated polymer coating, a halogenated wax coating, or a combination thereof. Non-limiting examples of halogenated polymer coatings include fluorinated halogenated polymers such as polytetrafluoroethylene (PTFE, sold under the tradename Teflon® by DuPont). Non-limiting examples of halogenated wax coatings include fluorinated waxes, chlorinated waxes, brominated waxes, and combinations thereof. Various commercial sources for halogenated waxes exist such as Dover Chemical Corporation (Dover, Ohio) which sells Doverguard® brand brominated waxes and Chlorez® brand chlorinated waxes. Use of the foregoing materials of construction for the support structure or employing those materials as a coating for the support structure upon which the layers are formed can facilitate the processes of the first-fourth embodiments and production of the resulting products by enabling the product to be more easily removed from the support structure, preferably without curing or otherwise sticking to the support structure such that removal therefrom involves tearing or breaking one or more layers of the product. As those of skill in the art will appreciate, the particular material(s) of construction used for the support structure may be intentionally varied depending upon the ingredients contained in the rubber particles, the liquid binder (e.g., the actinic radiation curable polymeric mixture), or both.

Rubber Particles

As discussed above, according to the processes of the first-fourth embodiments, the rubber particles that are used to form the first rubber layer and any additional rubber layers comprise (include) at least one conjugated diene monomer-containing polymer and reinforcing filler. In preferred embodiments of the processes of the first-fourth embodiments, the rubber particles are an integral mixture of at least one conjugated diene monomer-containing polymer and reinforcing filler; in other words, in such embodiments the reinforcing filler is mixed throughout the conjugated diene monomer-containing polymer. As those of skill in the art will appreciate, various methods exist for producing rubber particles that are an integral mixture of at least one conjugated diene monomer-containing polymer, including, but not limited to mixing or compounding together the at least one conjugated diene monomer-containing polymer along with any reinforcing filler in a blender or other mechanical mixer so as to disperse the reinforcing filler throughout the polymer. Mixing or compounding together of the at least one conjugated diene monomer-containing polymer along with any reinforcing filler constitutes a preferred method of forming rubber particles when virgin or unused rubber polymer is utilized for the rubber particles. After sufficient mixing, rubber particles may be produced from the solid rubber mixture that results by methods such as grinding, grating, or crushing; certain such methods may include low temperature (e.g., cryogenic with liquid nitrogen) freezing of the solid rubber prior to grinding, grating or crushing. Alternatively, the rubber particles may be produced from recycled rubber products (e.g., used tires or tire components such as retreads) which already contain at least one conjugated diene monomer-containing polymer mixed with reinforcing filler (e.g., carbon black). Various methods exist for producing rubber particles from recycled rubber products, including, but not limited to, cryogenic freezing and grinding of the frozen rubber. Exemplary manufacturers of rubber particles that may be utilized in certain embodiments of the first-fourth embodiments include, but are not limited to Lehigh Technologies, LLC (offering ground rubber under the PolyDyne™ brandname in various mesh sizes including 40, 80, 140 and 200), Edge Rubber (offering various rubber powders), and Genan Holding A/S (offering various rubber powders).

According to the processes of the first-fourth embodiments, the at least one conjugated diene monomer-containing polymer of the rubber particles may be cured or alternatively may be uncured. In certain embodiments of the first-fourth embodiments, the rubber particles comprise at least one uncured conjugated diene monomer-containing polymer; in certain such embodiments, the only conjugated diene monomer-containing polymer(s) of the rubber particles are uncured (i.e., no cured conjugated diene monomer-containing polymers are contained within the rubber particles as they are used in the processes to form rubber layers). In other embodiments of the first-fourth embodiments, the rubber particles comprise at least one cured conjugated diene monomer-containing polymer; in certain such embodiments, the only conjugated diene monomer-containing polymer(s) of the rubber particles are cured (i.e., no uncured conjugated diene monomer-containing polymers are contained within the rubber particles as they are used in the processes to form rubber layers). As mentioned above, a potential source of rubber particles comprising at least one cured conjugated diene monomer-containing polymer are used or recycled rubber goods; however, such should not be considered the only source for cured polymer.

According to the processes of the first-fourth embodiments, the particular conjugated diene monomer-containing polymer or polymers present in the rubber particles may vary. The phrase conjugated diene monomer-containing polymer is used to refer to a polymer that comprises (is based upon) at least one conjugated diene monomer. A conjugated diene monomer is a monomer having two carbon-carbon double bonds separated by a single carbon-carbon bond. Various conjugated diene monomers exist and are generally suitable for use in preparing the conjugated diene monomer-containing polymer(s). In certain embodiments according to the first-fourth embodiments disclosed herein, the at least one conjugated diene monomer-containing polymer of the rubber particles comprises monomers selected from at least one of: acyclic and cyclic dienes having 3 to about 15 carbon atoms. In certain embodiments according to the first-fourth embodiments disclosed herein, the at least one conjugated diene monomer-containing polymer of the rubber particles comprises monomers selected from at least one of: 1,3-butadiene, isoprene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, 2,4-hexadiene, 1,3-cyclopentadiene, 1,3-cyclohexadiene, 1,3-cycloheptadiene, and 1,3-cyclooctadiene, farnescene, and substituted derivatives of each of the foregoing. In certain embodiments of the first-fourth embodiments, the at least one conjugated diene monomer-containing polymer of the rubber particles comprises 1,3-butadiene monomer, isoprene monomer, or a combination thereof. In certain embodiments of the first-fourth embodiments, the at least one conjugated diene monomer-containing polymer of the rubber particles further comprises (i.e., in combination with the at least one conjugated diene monomer) at least one vinyl aromatic monomer. Non-limiting examples of suitable vinyl aromatic monomers include, but are not limited to, styrene, α-methyl styrene, p-methylstyrene, o-methylstyrene, p-butylstyrene, vinylnaphthalene, p-tertbutylstyrene, vinyl catechol-based, and combinations thereof. In certain embodiments of the first-fourth embodiments, the at least one conjugated diene monomer-containing polymer of the rubber particles comprises a combination of 1,3-butadiene monomer and styrene monomer. In certain embodiments of the first-fourth embodiments, the at least one conjugated diene monomer-containing polymer of the rubber particles comprises at least one of the following: natural rubber, polyisoprene, styrene-butadiene rubber, polybutadiene rubber, styrene-isoprene rubber, butadiene-isoprene-rubber, styrene-isoprene-butadiene rubber, or farnasene co-polymers of the foregoing. In certain embodiments of the first-fourth embodiments, the at least one conjugated diene monomer-containing polymer of the rubber particles consists of at least one of the following: natural rubber, polyisoprene, styrene-butadiene rubber, polybutadiene rubber, styrene-isoprene rubber, butadiene-isoprene-rubber, or styrene-isoprene-butadiene rubber, or farnasene co-polymers of the foregoing; in certain such embodiments the only rubber present in the rubber particles is one or more the foregoing rubbers.

According to the first-fourth embodiments disclosed herein, the number average molecular weight (Mn) of the at least one conjugated diene monomer-containing polymer of the rubber particles may vary. In certain embodiments of the first-fourth embodiments disclosed herein, the at least one conjugated diene monomer-containing polymer of the rubber particles is a synthetic polymer having a Mn of 80,000 to 1,000,000, preferably 100,000 to 500,000 grams/mole. The Mn values referred to herein are number average molecular weights which can be determined by using gel permeation chromatography (GPC) calibrated with polystyrene standards and Mark-Houwink constants for the polymer in question.

According to the processes of the first-fourth embodiments, the size of the rubber particles used to form the rubber layers may vary. In certain embodiments of the first-fourth embodiments, the rubber particles have an average particle size of about 10 microns to about 1000 microns (e.g., 10 microns to 1000 microns, about 10 microns to about 900 microns, 10 microns to 900 microns, about 10 microns to about 800 microns, 10 microns to 800 microns, about 10 microns to about 700 microns, 10 microns to 700 microns, about 10 microns to about 600 microns, 10 microns to 600 microns, about 10 microns to about 500 microns, 10 microns to 500 microns, about 10 microns to about 400 microns, 10 microns to 400 microns, about 10 microns to about 300 microns, 10 microns to 300 microns, about 10 microns to about 200 microns, 10 microns to 200 microns, about 10 microns to about 100 microns, or 10 microns to 100 microns). In certain preferred embodiments of the processes of the first-fourth embodiments, the average particle size of the rubber particles is determined by sieve analysis (e.g., according to ASTM D5603 or ASTM D5644). Generally, the average particles size of rubber particles can be determined by sieve analysis using multiple sieves through which a measured quantity of rubber particles is sequentially passed with the amount retained on each screen of a sieve being weighed and the result given as a percentage of sample retained on each; thereafter, the various percentages retained can be used to obtain an average particle size. In certain embodiments of the first-fourth embodiments, at least 95%, at least 98%, at least 99%, or 100% by weight of the rubber particles have particle sizes in one of the foregoing ranges. In certain embodiments of the first-fourth embodiments, the rubber particles have an average particle size of about 10 microns to about 500 microns (e.g., 10 microns to 500 microns). In certain embodiments of the first-fourth embodiments, the rubber particles used to form the rubber layers are in powder form and have an average particle size according to one of the preceding ranges. It should be understood that the phrase powder form is used to refer to rubber particles that are in a loose form; generally, powders will be capable of freely flowing (such as from a dispensing device) and/or once accumulated into a layer or pile upon a surface will be capable of being dislodged by the application of an air stream or by tilting the surface upside down. In certain embodiments of the first-fourth embodiments, the rubber particles are 18 mesh in size or smaller, 35 mesh in size or smaller, 60 mesh in size or smaller, 100 mesh in size or smaller, or 200 mesh in size or smaller. By listing a mesh size as "X mesh" or smaller is meant that the particles pass through a mesh screen of X mesh size; such particles may alternatively be described as X mesh particles.

In certain embodiments of the first-fourth embodiments, the rubber particles in powder form comprise at least one cured conjugated diene-monomer containing polymer. In certain embodiments of the first-fourth embodiments, the rubber particles used to form the rubber layers are in paste form and have an average particle size according to one of the preceding ranges. In certain embodiments of the first-fourth embodiments, the rubber particles in paste form are combined with one or more resins. In certain such embodiments, the one or more resins may be present in an integral mixture with the least one conjugated diene monomer-containing polymer and reinforcing filler; in other words, in such embodiments the resin filler is mixed throughout the conjugated diene monomer-containing polymer and filler. In other embodiments, the rubber particles may be mixed throughout the one or more resins to form a paste of rubber particles and resin. It should be understood that the phrase paste form is used to refer to a thick, moist substance that contains the rubber particles, generally a paste will be spreadable upon a surface, but will not be capable of being dislodged by the application of an air stream or by tilting the surface upside down. In certain embodiments of the first-fourth embodiments, the rubber particles in paste form can also be considered to be a gel. In certain embodiments of the first-fourth embodiments, the rubber particles in paste form comprise at least one uncured conjugated diene-monomer containing polymer.

As discussed above, according to processes of the first-fourth embodiments the rubber particles that are used to form the first rubber layer and any additional rubber layers comprise (include) reinforcing filler. The term "reinforcing filler" is used herein to refer to a particulate material that has a nitrogen absorption specific surface area ($N_2SA$) of about 20 $m^2/g$ or greater, including 20 $m^2/g$ or greater, more than about 50 $m^2/g$, more than 50 $m^2/g$, more than about 100 $m^2/g$, more than 100 $m^2/g$, more than about 125 $m^2/g$, and more than 125 $m^2/g$. In certain embodiments, the term "reinforcing filler" is alternatively or additionally used to refer to a particulate material that has a particle size of about 10 nm up to about 1000 nm, including 10 nm up to 1000 nm, about 10 nm up to about 50 nm, and 10 nm up to 50 nm. In preferred embodiments of the first-fourth embodiments, the reinforcing filler(s) of the rubber particles is/are integrally mixed with the polymer of the rubber particles. In certain embodiments of the first-fourth embodiments, the reinforcing filler of the rubber particles comprises carbon black, silica, or a combination thereof. In certain embodiments of the first-fourth embodiments, the reinforcing filler of the rubber particles consists of carbon black, silica, or a combination thereof. In certain embodiments of the first-fourth embodiments, the reinforcing filler comprises at least one of the following (preferably in combination with carbon black, silica, or a combination thereof): alumina, aluminum hydroxide, clay, magnesium hydroxide, boron nitride, aluminum nitride, titanium dioxide, reinforcing zinc oxide, and combinations thereof. In certain embodiments of the first-fourth embodiments, the rubber particles include at least one of the following fillers: talc, clay, starch, alumina ($Al_2O_3$), aluminum hydrate ($Al_2O_3H_2O$), aluminum hydroxide ($Al(OH)_3$), aluminum carbonate ($Al_2(CO_3)_2$), aluminum nitride, aluminum magnesium oxide ($MgOAl_2O_3$), pyrofilite ($Al_2O_3 4SiO_2.H_2O$), bentonite ($Al_2O_3.4SiO_2.2H_2O$), boron nitride, mica, kaolin, glass balloon, glass beads, calcium oxide (CaO), calcium hydroxide ($Ca(OH)_2$), calcium carbonate ($CaCO_3$), magnesium carbonate, magnesium hydroxide ($MH(OH)_2$), magnesium oxide (MgO), magnesium carbonate ($MgCO_3$), titanium oxide, titanium dioxide, potassium titanate, barium sulfate, zirconium oxide ($ZrO_2$), zirconium hydroxide [$Zr(OH)_2.nH_2O$], zirconium carbonate

[Zr(CO$_3$)$_2$], crystalline aluminosilicates, reinforcing grades of zinc oxide (i.e., reinforcing zinc oxide), and combinations thereof. In certain embodiments of the first-fourth embodiments, the reinforcing filler comprises at least one of the foregoing wherein the filler is nano-sized.

According to the processes of the first-fourth embodiments, the amount of reinforcing filler(s) in the rubber particles may vary. Generally, the amount of reinforcing filler(s) can be measured based upon 100 parts of polymer/rubber (i.e., the conjugated diene monomer-containing polymer) and is denoted in phr (parts per hundred rubber) or as a weight % based upon the total weight of the rubber particles. In certain embodiments, of the first-fourth embodiments, the rubber particles comprise 10 to 200 phr of reinforcing filler (e.g., 10, 20, 30, 40, 50, 60, 70, 80, 90, 100, 110, 120, 130, 140, 150, 160, 170, 180, 190, or 200 phr), preferably 20 to 150 phr of reinforcing filler or 30 to 100 phr of reinforcing filler (when more than one reinforcing filler is utilized, the foregoing amounts should be understood to refer to the total amount of all reinforcing fillers).

In those embodiments of the first-fourth embodiments wherein the rubber particles include carbon black as reinforcing filler, the particular carbon black(s) used may vary as can the amount of each. In certain embodiments of the first-fourth embodiments, the rubber particles comprise 5 to 200 phr of reinforcing carbon black filler (e.g., 5, 10, 20, 30, 40, 50, 60, 70, 80, 90, 100, 110, 120, 130, 140, 150, 160, 170, 180, 190, or 200 phr) or 10 to 100 phr of reinforcing carbon black filler. In certain embodiments of the first-fourth embodiments, the rubber particles comprise about 10 to about 50% by weight carbon black reinforcing filler, 10-50% (e.g., 10%, 12%, 15%, 17%, 20%, 22%, 25%, 27%, 30%, 32%, 35%, 37%, 40%, 42%, 45%, 47%, 50%) by weight carbon black reinforcing filler, about 20 to about 40% by weight carbon black reinforcing filler, 20-40% by weight carbon black reinforcing filler, about 25 to about 35% by weight carbon black reinforcing filler, or 25-35% by weight carbon black reinforcing filler (the foregoing weight percentages based upon the total weight of the rubber particles). In certain embodiments of the first-fourth embodiments, wherein the reinforcing filler of the rubber particles comprises carbon black, preferably in an amount of about 20 to about 40% by weight of the rubber particles, the rubber particles further comprise at least one of: oil, stearic acid, sulfur, or zinc oxide. Generally, suitable carbon black filler for use in certain embodiments of the first-fourth embodiment disclosed herein includes any of the commonly available, commercially-produced carbon blacks, including those having a surface area of at least about 20 m$^2$/g (including at least 20 m$^2$/g) and, more preferably, at least about 35 m$^2$/g up to about 200 m$^2$/g or higher (including 35 m$^2$/g up to 200 m$^2$/g). Surface area values used in this application are determined by ASTM D-1765 using the cetyltrimethylammonium bromide (CTAB) technique. Among the useful carbon blacks are furnace black, channel blacks, and lamp blacks. More specifically, examples of useful carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which can be utilized include acetylene blacks. In certain embodiments of the first-fourth embodiment disclosed herein, the rubber composition includes a mixture of two or more of the foregoing blacks. Typical suitable carbon blacks for use in certain embodiments of the fourth embodiment disclosed herein are N-110, N-220, N-339, N-330, N-351, N-550, and N-660, as designated by ASTM D-1765-82a. The carbon blacks utilized can be in pelletized form or an unpelletized flocculent mass. Preferably, for more uniform mixing, unpelletized carbon black is preferred.

In those embodiments of the first-fourth embodiments wherein the rubber particles include silica as reinforcing filler, the particular silica(s) used may vary as can the amount of each. In certain embodiments of the first-fourth embodiments, the rubber particles comprise 5 to 200 phr of reinforcing silica filler (e.g., 5, 10, 20, 30, 40, 50, 60, 70, 80, 90, 100, 110, 120, 130, 140, 150, 160, 170, 180, 190, or 200 phr), or 10 to 100 phr of reinforcing silica filler. Suitable silica fillers for use in the rubber particles are well known. Non-limiting examples of silica fillers suitable for use in certain embodiments of the first-fourth embodiment disclosed herein include, but are not limited to, precipitated amorphous silica, wet silica (hydrated silicic acid), dry silica (anhydrous silicic acid), fumed silica, calcium silicate and the like. Other suitable silica fillers for use in certain embodiments of the first-fourth embodiment disclosed herein include, but are not limited to, aluminum silicate, magnesium silicate (Mg$_2$SiO$_4$, MgSiO$_3$ etc.), magnesium calcium silicate (CaMgSiO$_4$), calcium silicate (Ca$_2$SiO$_4$ etc.), aluminum silicate (Al$_2$SiO$_5$, Al$_4$.3SiO$_4$.5H$_2$O etc.), aluminum calcium silicate (Al$_2$O$_3$.CaO$_2$SiO$_2$, etc.), and the like. Among the listed silica fillers, precipitated amorphous wet-process, hydrated silica fillers are preferred. Such silica fillers are produced by a chemical reaction in water, from which they are precipitated as ultrafine, spherical particles, with primary particles strongly associated into aggregates, which in turn combine less strongly into agglomerates. The surface area, as measured by the BET method, is a preferred measurement for characterizing the reinforcing character of different silica fillers. In certain embodiments of the first-fourth embodiments disclosed herein, the rubber particles comprise a silica filler having a surface area (as measured by the BET method) of about 32 m$^2$/g to about 400 m$^2$/g (including 32 m$^2$/g to 400 m$^2$/g), with the range of about 100 m$^2$/g to about 300 m$^2$/g (including 100 m$^2$/g to 300 m$^2$/g) being preferred, and the range of about 150 m$^2$/g to about 220 m$^2$/g (including 150 m$^2$/g to 220 m$^2$/g) being included. In certain embodiments of the first-fourth embodiments disclosed herein, the rubber particles comprise silica filler having a pH of about 5.5 to about 7 or slightly over 7, preferably about 5.5 to about 6.8. Some of the commercially available silica fillers which can be used in the rubber particles of certain embodiments of the first-fourth embodiment disclosed herein include, but are not limited to, Hi-Sil® 190, Hi-Sil® 210, Hi-Sil® 215, Hi-Sil® 233, Hi-Sil® 243, and the like, produced by PPG Industries (Pittsburgh, Pa.). As well, a number of useful commercial grades of different silica fillers are also available from Degussa Corporation (e.g., VN2, VN3), Rhone Poulenc (e.g., Zeosil™ 1165 MP), and J. M. Huber Corporation.

In certain embodiments of the first-fourth embodiments disclosed herein, the silica filler comprises a silica that has been pre-reacted with a silica coupling agent; preferably the pre-treated silica comprises a silica that has been pre-treated with a silane-containing silica coupling agent. In other embodiments of the first-fourth embodiments disclosed herein the silica filler of the rubber particles is used in combination with at least one silica coupling agent. In certain embodiments of the first-fourth embodiments disclosed herein, the silica coupling agent is present in an amount sufficient to provide a ratio of the total amount of silica coupling agent to silica filler of about 1:100 to about 1:5 (i.e., about 0.01 to about 20 parts by weight per 100 parts of silica), including 1:100 to 1:5, about 1:100 to about 1:10, 1:100 to 1:10, about 1:100 to about 1:20, 1:100 to 1:20, about 1:100 to about 1:25, and 1:100 to 1:25 as well as about 1:100 to about 0:100 and 1:100 to 0:100. In certain embodiments according to the first-fourth embodiments, the rubber particles comprise about 0.01 to about 10 phr silica coupling agent, including 0.01 to 10 phr, about 0.01 to about 5 phr, 0.01 to 5 phr, about 0.01 to about 3 phr, and 0.01 to 3 phr.

In certain embodiments of the first-fourth embodiments, the rubber particles that are used to form the first rubber layer and any additional rubber layers further comprise (include) at least one resin. In preferred embodiments of the first-fourth embodiments, the resin(s) of the rubber particles is/are integrally mixed with the polymer of the rubber particles. The type or chemical composition of the at least one resin that is included in the rubber particles may vary. In certain embodiments of the first-fourth embodiments, the at least one resin of the rubber particles comprises at least one of the following: phenolic resin(s), aliphatic resin(s), cycloaliphatic resin(s), aromatic resin(s), terpene resin(s), rosin resin(s), or guayule resin(s). Each of these resins is discussed in more detail below. In certain embodiments of the first-fourth embodiments, the rubber particles are free of or do not contain (i.e., have 0 phr) of any of the foregoing resins.

In those embodiments of the first-fourth embodiments where the rubber particles further comprise (include) at least one resin, the amount of resin may vary. In certain embodiments of the first-fourth embodiments, the rubber particles comprise 1 to 100 phr of at least one resin (e.g., 1, 5, 10, 15, 20, 25, 30, 35, 40, 45, 50, 55, 60, 65, 70, 75, 80, 85, 90, 95, 100 phr), 5 to 50 phr of at least one resin, or 5 to 25 phr of at least one resin. In those embodiments where more than one resin is contained in the rubber particles, the foregoing amounts should be understood to refer to the total amount of resins. In certain embodiments of the first-fourth embodiments, the rubber particles comprise at least one reinforcing filler and at least one resin with the amount of resin being no more than 50%, no more than 40%, no more than 30%, or no more than 20% by weight of the amount of filler. As a non-limiting example, if the rubber particles included 50 phr of reinforcing carbon black filler and the amount of resin was no more than 30% be weight of the amount of filler the amount of resin would be no more than 15 phr (e.g., 1 phr, 5, phr, 10 phr, 15 phr).

In certain embodiments of the first-fourth embodiments, the rubber particles further comprise (include) at least one of oil, stearic acid, sulfur or zinc oxide; in certain such embodiments, the foregoing ingredients (as well as reinforcing filler such as carbon black) are present in the rubber particles as a result of utilizing recycled tire components as a source of the rubber particles. In certain embodiments of the first-fourth embodiments, the rubber particles further comprise (include) oil, stearic acid, sulfur, and zinc oxide. According to the first-fourth embodiments, when oil, stearic acid, sulfur and/or zinc oxide are present in the rubber particles, the amount of each may vary. In certain embodiments of the first-fourth embodiments, the rubber particles further comprise (include) at least one oil in an amount of about 5 to about 25% by weight, 5-25% (e.g., 5%, 7%, 10%, 12%, 15%, 17%, 20%, 22%, 25%) by weight, about 10 to about 20% by weight, or 10-20% by weight (the foregoing amounts based upon the total weight of the rubber particles). In certain embodiments of the first-fourth embodiments, the rubber particles further comprise (include) stearic acid in an amount of about 0.5 to about 3% by weight, 0.5-3% (e.g., 0.5%, 1%, 1.5%, 2%, 2.5%, 3%) by weight, about 1 to about 2% by weight, or 1-2% by weight (the foregoing amounts based upon the total weight of the rubber particles). In certain embodiments of the first-fourth embodiments, the rubber particles further comprise (include) sulfur in an amount of about 1 to about 5% by weight, 1-5% (e.g., 1%, 1.5%, 2%, 2.5%, 3%, 3.5%, 4%, 4.5%, 5%) by weight, about 1 to about 3% by weight, or 1-3% by weight (the foregoing amounts based upon the total weight of the rubber particles). In certain embodiments of the first-fourth embodiments, the rubber particles further comprise (include) zinc oxide in an amount of about 1 to about 5% by weight, 1-5% (e.g., 1%, 1.5%, 2%, 2.5%, 3%, 3.5%, 4%, 4.5%, 5%) by weight, about 2 to about 3% by weight, or 2-3% by weight (the foregoing amounts based upon the total weight of the rubber particles). In certain embodiments of the first, third and fourth embodiments, the rubber particles comprise 10-50% by weight carbon black reinforcing filler, 5-25% by weight oil, and 30-50% by weight cured rubber.

Forming Rubber Particles into Rubber Layer(s)

As discussed above, the processes of the first-fourth embodiments include forming rubber particles into a first rubber layer upon the support structure as well as sequentially forming additional rubber layers upon the first bound layer (the additional rubber layers also being formed from rubber particles). By stating that additional rubber layers are sequentially formed upon the first bound layer is meant that a first rubber layer is formed, liquid binder is applied to that first rubber layer forming a first bound layer, a second rubber layer is formed (from rubber particles) upon the upper surface of the first bound layer, liquid binder is applied to (the upper surface of) that second rubber layer forming a second bound layer, a third rubber layer is formed (from rubber particles) upon the upper surface of the second bound layer, liquid binder is applied to (the upper surface of that third rubber layer forming a third bound layer, etc. (i.e., fourth, fifth, sixth and further layers formed); in certain such embodiments some of the applications of liquid binder can be omitted. In certain embodiments of the first-fourth embodiments wherein omission of some of the applications of liquid binder occurs, the rubber particles are in a paste or gel form. Moreover, as discussed in more detail below, in certain embodiments the processes of the first-fourth embodiments are modified such that the application of liquid binder to the first rubber layer and/or the additional rubber layers can either be reduced in quantity or eliminated entirely if the rubber particles mixed with liquid binder prior to being formed into rubber layers in the actinic manufacturing device. As discussed in more detail below, according to the processes of the first-fourth embodiments, curing is effected by applying actinic radiation, heat, or a combination thereof to one or more of the bound layers; according to such processes it should be understood that the actinic radiation, heat, or a combination thereof may be applied to each of the bound layers (i.e., after application of liquid binder to the rubber layer to form the bound layer but prior to formation of the next rubber layer upon the surface of the bound layer) or may be applied to less than each bound layer individually (i.e., not necessarily after each application of liquid binder and not necessarily prior to each formation of a subsequent rubber layer).

In certain embodiments of the first-fourth embodiments, the forming of rubber layers (i.e., the first rubber layer as well as additional rubber layers) includes distributing of the rubber particles into a layer on the support structure followed by flattening of the rubber layer to achieve a desired thickness throughout the rubber layer; such flattening may be particularly useful when the rubber particles used to form the rubber layer(s) are in powder form. Generally, such flattening will achieve a smooth rubber layer which has a thickness that varies by no more than +/−8%, no more than +/−5% (even more preferably no more than +/−3%, no more than +/−2% or even no more than +/−1%) throughout the layer. In those embodiments of the first-fourth embodiments wherein the rubber layer is flattened to achieve a desired thickness, the particular method used to flatten the rubber layer is not particularly limited and exemplary methods include the use of a blade, roller, or a wiper. In other embodiments of the first-fourth embodiments, the forming of rubber layers (i.e., the first rubber layer as well as additional rubber layers) includes distributing of the rubber particles into a layer on the support structure followed by spreading of the rubber layer to achieve a desired thickness throughout the rubber layer; such spreading may be particularly useful when the rubber particles used to form the rubber layer(s) are in paste form. Generally, such spreading will achieve a smooth rubber layer which has a thickness that varies by no more than +/−8%, no more than +/−5% (even more preferably no more than +/−3%, no more than +/−2% or even no more than +/−1%) throughout the layer. In those embodiments of the first-fourth embodiments wherein the rubber layer is spread to achieve a desired thickness, the particular method used to flatten the rubber layer is not particularly limited and exemplary methods include the use of a press, a roller, or a combination thereof.

According to the first-fourth embodiments, the thickness of the rubber layers that are formed from rubber particles may vary. Generally, the thickness of a given rubber layer will be substantially the same as (i.e., with 85% of, or even within 90% of) the thickness of the bound layer that results therefrom. In certain embodiments of the first-fourth embodiments, the rubber layers that are formed from rubber particles have a thickness of about 10 microns to about 1000 microns (e.g., 10 microns to 1000 microns, about 10 microns to about 900 microns, 10 microns to 900 microns, about 10 microns to about 800 microns, 10 microns to 800 microns, about 10 microns to about 700 microns, 10 microns to 700 microns, about 10 microns to about 600 microns, 10 microns to 600 microns, about 10 microns to about 500 microns, 10 microns to 500 microns, about 10 microns to about 400 microns, 10 microns to 400 microns, about 10 microns to about 300 microns, 10 microns to 300 microns, about 10 microns to about 200 microns, 10 microns to 200 microns, about 10 microns to about 100 microns, or 10 microns to 100 microns). In certain embodiments of the first-fourth embodiments, the rubber layers that are formed from rubber particles have an average particle size of about 8.5 microns to about 850 microns (e.g., 8.5 microns to 850 microns) or about 8.5 microns to about 475 microns (e.g., 8.5 microns to 475 microns). In certain embodiments of the first-fourth embodiments, the rubber layers that are formed from rubber particles have an average particle size of about 10 microns to about 500 microns (e.g., 10 microns to 500 microns). According to the first-fourth embodiments, each rubber layer that is formed during the process of producing a cured polymeric product need not have the same thickness, although in certain embodiments, each rubber layer may have substantially the same thickness (i.e., varying by no more than +/−10%). In certain embodiments of the first-fourth embodiments, each bound layer has a thickness of about 10 to about 1000 microns (e.g., 10 microns to 1000 microns, about 10 microns to about 900 microns, 10 microns to 900 microns, about 10 microns to about 800 microns, 10 microns to 800 microns, about 10 microns to about 700 microns, 10 microns to 700 microns, about 10 microns to about 600 microns, 10 microns to 600 microns, about 10 microns to about 500 microns, 10 microns to 500 microns, about 10 microns to about 400 microns, 10 microns to 400 microns, about 10 microns to about 300 microns, 10 microns to 300 microns, about 10 microns to about 200 microns, 10 microns to 200 microns, about 10 microns to about 100 microns, or 10 microns to 100 microns).

In certain embodiments of the first-fourth embodiments, forming of the rubber particles into layers (e.g., the first rubber layer or additional rubber layers) comprises selective distribution of the rubber particles onto the support structure or onto the previously formed bound layer. In other words, in such embodiments, the rubber particles may be distributed over less than the entire cross-sectional area of the particular layer being formed so as to result in a layer or layers which may have hollows, voids or other spaces within. In other embodiments of the first-fourth embodiments, forming of the rubber particles into layers (e.g., the first rubber layer or additional rubber layers) comprises distribution of the rubber particles onto the support structure over the entire cross-sectional area of the particular layer being formed (without any hollows, void or other spaces within); in certain such embodiments any hollows, voids or other spaces sought to be formed with the particular layer may be formed by selective application of the liquid binder to less than the entire rubber layer of certain layer(s).

Liquid Binder

As discussed above, the processes of the first-fourth embodiments comprise (include) applying of liquid binder to the rubber layers wherein the liquid binder comprises a curable polymeric mixture and optionally a cure package. In certain embodiments of the first-fourth embodiments, the cure package is present in the liquid binder. By stating that the binder is a liquid binder is meant that the binder is capable of flowing or otherwise emerging or being dispensed from a storage container (e.g., a tank) onto the rubber layers; preferably the liquid binder is liquid at room temperature (i.e., 25° C.), but in certain embodiments the liquid binder may be a solid at room temperature but a liquid at an elevated temperature (e.g., above 25° C. such as 30, 40 50, 60 or 70 C up to about 120° C.). In certain embodiments of the first-fourth embodiments, the liquid binder is dispensed from the storage container via a nozzle, syringe or print head. In certain embodiments of the first-fourth embodiments, the liquid binder is selectively applied to less than the entire rubber layer of certain layer(s); in such embodiments, it should be appreciated that the liquid binder is applied to the entire rubber layer of other rubber layer(s). In certain embodiments of the first-fourth embodiments wherein the liquid binder is selectively applied to less than the entire rubber layer of certain layer(s), the actinic radiation is applied to the entirety of the bound layers (i.e., the entire surface); in such embodiments, it can be appreciated that only those areas of the rubber layer to which liquid binder has been applied will cure.

According to the first-fourth embodiments, the composition of the liquid binder, including the curable polymeric mixture of the liquid binder may vary. In certain embodiments of the first-fourth embodiments, the curable polymeric mixture comprises at least one of: UV curable resin, IR curable resin, heat curable resin, thermoset polymer, thermoplastic polymer, or thermoplastic elastomer. In certain embodiments of the first-fourth embodiments, the curable polymeric mixture of the liquid binder comprises one or more resins (e.g., without any polymer). In other embodiments of the first-fourth embodiments, the curable polymeric mixture of the liquid binder comprises one or more polymers (e.g., without any resin). In yet other embodiments of the first-fourth embodiments, the curable polymeric mixture of the liquid binder comprises a combination of one or more polymers and one or more resins.

In certain embodiments of the first-fourth embodiments, the curable polymeric mixture of the liquid binder comprises at least one thermoset polymer. As used herein, the term "thermoset" as in the phrase "thermoset polymer" is used to indicate a polymer which after curing does not soften upon heating. In certain embodiments of the first-fourth embodiments, the curable polymeric mixture comprises at least one thermoset polymer and excludes any thermoplastic polymer or thermoplastic elastomer. Exemplary thermoset polymers include the following: olefins (e.g., conjugated diene monomer-containing polymers such as high-cis (92% or higher) polybutadiene; styrene-butadiene copolymer; natural rubber; and polyisoprene), urethanes, phenol-formaldehydes, urea-formaldehydes, polyimides, cyanates (e.g., cyanate esters, polycyanurates), and polyesters.

In certain embodiments of the first-fourth embodiments, the curable polymeric mixture of the liquid binder comprises at least one thermoplastic polymer. As used herein the term "thermoplastic" as in the phrase "thermoplastic polymer" is used to indicate a polymer which softens upon heating and can generally be molded or shaped in its softened state. In certain embodiments of the first-fourth embodiments, the curable polymeric mixture comprises at least one thermoplastic polymer and excludes any thermoset polymer. Exemplary thermoplastic polymers include the following: acrylics (e.g., polyacrylate, poly(meth)acrylate), nitriles (e.g., acrylonitrile butadiene styrene or ABS), polyamides (e.g., nylon), aliphatic polyesters (e.g., polylactic acid or PLA), polycarbonates, polyethers (e.g., polyether sulfone or PES; polyetherether ketone or PEEK; or polyetherimide or PEI), polyethylenes, polyphenylenes (polyphenylene oxide or PPO, or polyphenylene sulfide or PPS), polypropylenes, polystyrenes, polyvinyl chloride (PVC), or fluoropolymers (e.g., polytetrafluoroethylene (PTFE).

In certain embodiments of the first-fourth embodiments, the curable polymeric mixture of the liquid binder comprises at least one thermoplastic elastomer. Thermoplastic elastomers are also known as thermoplastic rubbers. As used herein the phrase "thermoplastic elastomer" refers to a copolymer mixture of polymers (usually a plastic and a rubber) which consist of materials with both thermoplastic and elastomeric properties. Exemplary thermoplastic elastomers include the following: styrenic block copolymers (e.g., styrene-butadiene copolymers), thermoplastic olefins, elastomeric alloys, thermoplastic polyurethanes, thermoplastic copolyesters, and thermoplastic polyamides.

Actinic Radiation Curable Polymeric Mixture

In certain embodiments of the first-fourth embodiments, the curable polymeric mixture of the liquid binder comprises an actinic radiation curable polymeric mixture, optionally in combination with a cure package. As used herein, the phrase "actinic radiation curable polymeric mixture" refers to a mixture which can be cured using actinic radiation. In certain embodiments of the first-fourth embodiments, the actinic radiation curable polymeric mixture comprises: (a) a polyfunctionalized diene monomer-containing polymer having the formula: $[P][F]_n$ wherein P represents a diene monomer-containing polymer chain, F represents a functional group, n is 2 to about 15 (e.g., 2, 3, 4, 5, 6, 7, 8 9, 10, 11, 12, 13, 14 or 15), and each F can be the same or different; (b) optionally a chain extender based upon F or reactive with F; (c) at least one actinic radiation sensitive photoinitiator; (d) optionally a photosensitizer; and (e) a polyfunctional crosslinker reactive with F.

In certain embodiments according to the first-fourth embodiments, the total amount of (a) and (b) (i.e, polyfunctionalized diene monomer-containing polymer and chain extended based upon F or reactive with F (when present)) is 100 parts and (c) (i.e., actinic radiation sensitive photoinitiator) is present in a total amount of at least 0.1 parts (e.g., 0.1, 0.5, 1, 5, 10 parts), based upon 100 parts of (a) and (b), preferably (c) is present in a total amount of about 1 part to about 10 parts (e.g., 1, 2, 3, 4, 5, 6, 7, 8, 9, 10 parts), and at least one of the following is met: (i) the polyfunctionalized diene monomer-containing polymer (a) is present in an amount of 1-100 parts (e.g., 1, 5, 10, 15, 20, 25, 30, 35, 40, 45, 50, 55, 60, 65, 70, 75, 80, 85, 90, 95, 98, 99, or 100 parts) and (b) is present in an amount of 0-99 parts (e.g., 0, 1, 5, 10, 15, 20, 25, 30, 35, 40, 45, 50, 55, 60, 65, 70, 75, 80, 85, 90, 95, 99 parts); (ii) the photosensitizer (d) is present in an amount of about 0.1 parts to about 5 parts (e.g., 0.1, 0.2, 0.3, 0.4, 0.5, 0.6, 0.7, 0.8, 0.9, 1, 1.5, 2, 2.5, 3, 3.5, 4, 4.5, 5 parts), per 100 total parts of (a) and (b)); each F comprises at least one of: acrylate, methacrylate, cyanoacrylate, epoxide, aziridine, or thioepoxide; (iv) F comprises a free radical polymerizable functional group; (v) F comprises a cationic polymerizable functional group; (vi) the polyfunctionalized diene monomer-containing polymer (a) comprises a combination of cationic polymerizable and free radical polymerizable groups either on the same diene polymer chain or on separate diene polymer chains; (vii) the polyfunctionalized diene monomer-containing polymer (a) has a Mn of about 3,000 to about 135,000 grams/mole (e.g., 3,000; 5,000; 7,500; 10,000; 15,000; 20,000; 30,000; 40,000; 50,000; 60,000; 70,000; 80,000; 90,000; 100,000; 110,000; 120,000; 130,000; or 135,000 grams/mole), according to a polystyrene standard; (viii) the diene monomer-containing polymer chain comprises monomers selected from at least one of acyclic and cyclic diener having 3 to about 15 carbon atoms (e.g., 3, 4, 5, 6, 7, 8, 9, 10, 11, 12, 13, 14, 15 carbon atoms); (ix) the Tg of the polyfunctionalized diene monomer-containing polymer is about −105 to about −10 C (e.g., −105, −100, −90, −80, −70, −60, −50, −40, −30, −20, or 1-0 C); (x) the diene monomer-containing polymer chain comprises monomers selected from at least one of: 1,3-butadiene, isoprene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, 2,4-hexadiene, 1,3-cyclopentadiene, 1,3-cyclohexadiene, 1,3-cycloheptadiene, 1,3-cyclooctadiene, farnescene, and substituted derivatives of each of the foregoing; or (xi) in addition to (viii) above, the diene polymer chain further comprises at least one vinyl aromatic monomer. In certain embodiments according to the first-fourth embodiments, each of (i)-(x) is met. In other embodiments according to the first-fourth embodiments, each of (i)-(xi) is met.

In certain embodiments according to the first-fourth embodiments, the actinic radiation curable polymeric mixture is curable by light having a wavelength in the UV to Visible range. In certain embodiments of the first-fourth embodiments, the actinic radiation (light) has a wavelength of about 320 to less than 500 nm, including about 350 to about 450 nm, and about 365 to about 405 nm. Generally, there are two types of radiation induced curing chemistries: free radical and cationic. Free radical curing involves cross-linking through double bonds, most usually (meth)acrylate double bonds. Cationic curing involves cross-linking through other functional groups, most usually epoxy groups.

Polyfunctionalized Diene Monomer-Containing Polymer

As discussed above, the actinic radiation curable polymeric mixture comprises a polyfunctionalized diene monomer-containing polymer which comprises a diene polymer chain [P]. In certain embodiments of the first-fourth embodiments, the actinic radiation curable polymeric mixture comprises one type of polyfunctionalized diene monomer-containing polymer and in other embodiments, the mixture comprises more than one type of polyfunctionalized diene monomer-containing polymer. Polyfunctionalized diene monomer-containing polymers can be categorized into different types based upon one or more of: molecular weight, monomer type(s), relative amount of monomer(s), types of functional group(s) (e.g., free radical polymerizable or cationic polymerizable), identity of functional group(s) (as discussed in more detail below), and amount of functional group(s). In certain embodiments of the first-fourth embodiments, the polyfunctionalized diene monomer-containing polymer(s) can be referred to as a pre-polymer since they will react with each other and with a chain extender (when a chain extender is present) to form a higher molecular weight polymer. The diene polymer chain comprises (is based upon) at least one diene monomer. A diene monomer is a monomer having two carbon-carbon double bonds. Various diene monomers exist and are generally suitable for use in preparing the diene polymer chain of the polyfunctionalized diene monomer-containing polymer. In certain embodiments according to the first-fourth embodiments disclosed herein, the diene polymer chain of the polyfunctionalized diene monomer-containing polymer comprises monomers selected from at least one of: acyclic and cyclic diener having 3 to about 15 carbon atoms. In certain embodiments according to the first-fourth embodiments disclosed herein, the diene polymer chain of the polyfunctionalized diene monomer-containing polymer comprises monomers selected from at least one of: 1,3-butadiene, isoprene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, 2,4-hexadiene, 1,3-cyclopentadiene, 1,3-cyclohexadiene, 1,3-cycloheptadiene, and 1,3-cyclooctadiene, farnescene, and substituted derivatives of each of the foregoing. In certain embodiments of the first-fourth embodiments, the diene polymer chain of the polyfunctionalized diene monomer-containing polymer comprises 1,3-butadiene monomer, isoprene monomer, or a combination thereof. In certain embodiments of the first-fourth embodiments, the diene polymer chain of the polyfunctionalized diene-monomer-containing polymer further comprises at least one vinyl aromatic monomer. Non-limiting examples of suitable vinyl aromatic monomers include, but are not limited to, styrene, α-methyl styrene, p-methylstyrene, o-methylstyrene, p-butylstyrene, vinylnaphthalene, p-tertbutylstyrene, vinyl catechol-based, and combinations thereof. In certain embodiments of the first-fourth embodiments, the diene polymer chain of the polyfunctionalized diene monomer-containing polymer comprises a combination of 1,3-butadiene monomer and styrene monomer.

As discussed above, the term "polyfunctionalized" is used herein to refer to more than one functionalization and includes polymers that have been di-functionalized, tri-functionalized, etc. Generally, functionalization of a polymer may occur at one or both ends of a polymer chain, along the backbone of the polymer chain, and combinations thereof. Generally, each F functional group present in the polyfunctionalized diene monomer-containing polymer may be same or different. In certain embodiments according to the first-fourth embodiments disclosed herein, the polyfunctionalized diene monomer-containing polymer comprises a di-functionalized polymer having an F functional group at each terminal end of the polymer chain; each F functional group may be the same or different. In certain embodiments according to the first-fourth embodiments disclosed herein, the polyfunctionalized diene monomer-containing polymer comprises a di-functionalized polymer having a F functional group at one terminal end of the polymer chain and at least one additional F functional group along the backbone of the polymer chain; each F functional group may be the same or different. In certain embodiments according to the first-fourth embodiments disclosed herein, the polyfunctionalized diene monomer-containing polymer comprises a functionalized polymer having at least three F functional groups, with one at each terminal end of the polymer chain, and at least one along the backbone of the polymer chain; each F functional group may be the same or different.

Various polyfunctionalized diene monomer-containing polymers are commercially available and may be suitable for use in various embodiments of the first-fourth embodiments disclosed herein. Non-limiting examples of these include, but are not limited to, Sartomer CN307 polybutadiene dimethacrylate, Sartomer CN301 polybutadiene dimethacrylate and Sartomer CN303 hydrophobic acrylate ester, all available from Sartomer Americas (Exton, Pa.); Ricacryl® 3500 methacrylated polybutadiene, Ricacryl® 3801 methacrylated polybutadiene, Ricacryl® 3100 methacrylated polybutadiene, all available from Cray Valley USA LLC (Exton, Pa.); BAC-45 polybutadiene diacrylate and BAC-15 polybutadiene diacrylate, available from San Esters Corp. (New York, N.Y.); Kuraray UC-102 methacrylated polyisoprene and UC-203 methacrylated polyisoprene, available from Kuraray America Inc. (Pasadena, Tex.); Poly bd® 600E epoxidized polybutadiene and Poly bd® 605E polybutadiene, available from Cray Valley USA LLC (Exton, Pa.). Methods for preparing polyfunctionalized diene monomer-containing polymers are well-known to those of skill in the art and include those using functional initiators, functional terminators and reactions of diol terminated diener with various functional acid chlorides or with carboxylic acids (through a dehydration reaction). Other methods include the reaction of an oxidant and a carboxylic acid to form a peracid for adding an epoxy group.

In certain embodiments of the first-fourth embodiments, the diene polymer chain of the polyfunctionalized diene monomer-containing polymer comprises: polybutadiene, styrene-butadiene copolymer, polyisoprene, ethylene-propylene-diene rubber (EPDM), styrene-isoprene rubber, or butyl rubber (halogenated or non-halogenated). In certain embodiments of the first-fourth embodiments, the diene polymer chain of the polyfunctionzlied diene monomer-containing polymer consists of at least one conjugated diene monomer, optionally in combination with at least one vinyl aromatic monomer.

The molecular weight of the polyfunctionalized diene monomer-containing polymer may vary widely depending upon various factors, including, but not limited to the amount and type of chain extender (if any) that is utilized in the actinic radiation curable polymeric mixture. Generally, higher molecular weight polymers will lead to better properties in the cured article or product, but will also lead to higher viscosities in the overall actinic radiation curable polymeric mixture. Thus, preferred polyfunctionalized diene monomer-containing polymers for use in the mixture will balance molecular weight with its effect on viscosity. In certain embodiments of the first-fourth embodiments, the polyfunctionalized diene monomer-containing polymer has a Mn of about 3,000 to about 135,000 grams/mole (polystyrene standard). In certain embodiments of the first-fourth embodiments, the polyfunctionalized diene monomer-containing polymer has a Mn of 3,000 to 135,000 grams/mole (polystyrene standard); including about 5,000 to about 100,000 grams/mole (polystyrene standard); 5,000 to 100,000 grams/mole (polystyrene standard); about 10,000 to about 75,000 grams/mole (polystyrene standard); and 10,000 to 75,000 grams/mole (polystyrene standard). The number average molecular weights ($M_n$) values that are discussed herein for the polyfunctionalized diene monomer-containing polymer include the weight contributed by the functional groups (F).

In certain embodiments of the first-fourth embodiments, the cured polymeric product comprises crosslinked polyfunctionalized diene monomer-containing polymer having a Mc (molecular weight between crosslinks) of about 500 to about 150,000 grams/mole, including 500 to 150,000 grams/mole (e.g., 1000, 2500, 5000, 10000, 20000, 25000, 30000, 40000, 50000, 60000, 70000, 80000, 90000, 100000, 110000, 115000, 120000, 130000, 140000 or 150000). The crosslinked molecular weight ($M_c$) values that are discussed herein for the polyfunctionalized diene monomer-containing polymer include the weight contributed by the functional groups (F). $M_c$ can be determined in accordance with previously published procedures such as those disclosed in Hergenrother, J., Appl. Polym. Sci., v. 32, pp. 3039 (1986), herein incorporated by reference in its entirety.

In certain embodiments of the first-fourth embodiments, the molecular weight of the crosslinked polyfunctionalized diene monomer-containing polymer of the cured elastomeric mixture can be quantified in terms of $M_r$ or molecular weight between chain restrictions. In certain embodiments of the first-fourth, the cured elastomeric mixture comprises crosslinked polyfunctionalized diene monomer-containing polymer has a Mc (molecular weight between crosslinks) of about 500 to about 150,000 grams/mole, including 500 to 150,000 grams/mole (e.g., 1000, 2500, 5000, 10000, 20000, 25000, 30000, 40000, 50000, 60000, 70000, 80000, 90000, 100000, 110000, 115000, 120000, 130000, 140000 or 150000). The crosslinked molecular weight ($M_e$) values that are discussed herein for the polyfunctionalized diene monomer-containing polymer include the weight contributed by the functional groups (F). Generally, $M_r$ can be determined according to the procedure described in U.S. Patent Application Publication No. 2012/0174661, herein incorporated by reference in its entirely. More specifically, $M_r$ can be determined according to the following equation:

$$M_r = \frac{\rho RT(\Lambda - \Lambda^{-2})}{\sigma}$$

where ρ is the compound density, σ is stress, R is the gas constant, T is temperature, $\Lambda$ is 1+X∈ where X is the strain amplification factor from the Guth-Gold equation and the strain (∈) is $(I-I_{set})/I_{set}$ where I is the specimen length at a point on the retraction curve and $I_{set}$ is the specimen length after retraction to zero stress. A TR or tensile retraction test set consists of at least two tensile retraction tests, each to a progressively higher target extension ratio, $\Lambda$max, followed immediately by a retraction to a zero stress. Each tensile pull and subsequent retraction are performed at the same testing rate such that a series of extension and retraction curve pairs are obtained. During each retraction, the stress, σ, is measured as a function of extension ratio, $\Lambda$, defining the tensile retraction curve. Testing may be performed in accordance with the procedures outlined in Hergenrother, J., Appl. Polym. Sci., v. 32, pp. 3039 (1986), herein incorporated by reference in its entirety.

When determining $M_r$ for compounds containing rigid fillers, the enhancement of modulus due to rigid particles should be taken into account in a fashion similar to that of Harwood and Payne, J. Appl. Polym. Sci., v. 10, pp. 315 (1966) and Harwood, Mullins and Payne, J. Appl. Polym. Sci, v. 9, pp. 3011 (1965), both of which are herein incorporated by reference in their entirety. When a filled compound is first stretched in tension to the same stress as its corresponding gum compound (e.g., non-filled compound), subsequent retraction and extension curves are generally very similar to those of the gum compounds when stress is graphed as a function of normalized strain. Normalized strain is defined as the strain at any point on the subsequent extension or retraction curves divided by the maximum strain of the initial extension. For retraction curves in particular, and for maximum strains of natural rubber gum compounds up to and including near breaking strain, this could be applied to a number of filled compounds. The result can be interpreted as evidence of strain amplification of the polymer matrix by the filler, where the average strain in the polymer matrix of a filled compound is the same as that in the corresponding gum (non-filled) compound, when the filled and gum compounds are compared at the same stress. Strain amplification X can be determined by the Guth-Gold equation as discussed in Mullins et al., J. Appl. Polym. Sci., vol. 9, pp. 2993 (1965) and Guth et al., Phys. Rev. v. 53, pp. 322 (1938), both of which are herein incorporated by reference in their entirety. After correction of A for filler level, neo-Hookean rubber elasticity theory (Shen, Science & Technology of Rubber, Academic Press, New York, 1978, pp. 162-165, herein incorporated by reference) may be applied to an internal segment of the retraction curve from which a molecular weight between chain restrictions of all types, $M_r$ can be calculated according to the above equation. Extension of the same rubber specimen to successively higher $\Lambda$max provides $M_r$ as a function of $\Lambda$max.

Tensile retraction testing can be measured using a special ribbed TR mold to prevent slippage when stretched in tension between clamps of an Instron 1122 tester controlled by a computer (for testing, data acquisition and calculations), as described in Hergenrother, J., Appl. Polym. Sci., v. 32, pp. 3039 (1986). Specimens for testing may be nominally 12 mm wide by 50 mm long by 1.8 mm thick. $M_r$ can be calculated at each of 25 (σ, $\Lambda$) pairs, collected from about the middle one-third of the particular retraction curve. $M_r$ values as disclosed herein may be the average of the 25 calculated values. In order to reduce test time, elongations to successively higher $\Lambda$max can be carried out at successively higher speeds of the Instron crosshead motion. A master TR curve can be obtained by shifting the different test speeds to a standardized testing rate of 5%/minute. High strain (greater than about 40% to 80% elongation) region of the smooth curve obtained may be fitted by a linear equation of the form of $M_r$=S($\Lambda$max−1)+Mc. The fit to strain region at less than 80% elongation may deviate steadily from the $M_r$ line as strains are progressively reduced. The logarithim of such difference between the calculated and observed ve can be plotted versus the lower level of strain to give a linear fit to $\Delta$ve as a function of ($\Lambda$max−1). The antilog of the reciprocal of the intercept, m, can be denoted as B (expressed in kg/mole) and relates to the micro-dispersion of the filler. See, U.S. Pat. No. 6,384,117, herein incorporated by reference in its entirety. In a similar fashion, the lowest strain deviation can be treated to give a plot of $\Delta\Delta$ve as a function of ($\Lambda$max$-1$). The antilog of the reciprocal of the intercept for the process that occurs at strains of less than 6% elongation can be denoted as y (expressed in kg/mole). These three equations, each with a slope and intercept, can be used to fit the various strain regions of the TR curve can be summed to provide a single master equation that empirically describes the $M_r$ response over the entire range of testing. Experimental constants of the new master equation can be adjusted using ExcelSolver® to obtain the best possible fit of the predicted values to the experimental values obtained by TR. Fitting criteria consisting of a slope and an intercept can be determined when the experimental and curve fit values of $M_r$ are compared. The composite equation can allow the transition between each fitted linear region to be independent of the choice of the experimental strains measured and the small mathematical adjusting of the strain range can allow a more precise linear fit of the data to be made.

F Functional Groups

As discussed above, F represents a functional group associated with the polyfunctionalized diene monomer-containing polymer. Various types of functional groups F may be suitable for use in certain embodiments of the first-fourth embodiments disclosed herein. In certain embodiments of the first-fourth, these functional groups F can be described as either free radical polymerizable or cationic polymerizable, which is a general description of how the groups react upon exposure to actinic radiation (light) to result in cross-linking or curing. Generally, functional groups that improve curability (cross-linking) by actinic radiation are useful as the functional group F.

In certain embodiments of the first-fourth embodiments, the F functional group of the polyfunctionalized diene monomer-containing polymer comprises a free radical polymerizable functionalizing group. In certain embodiments of the first-fourth embodiments, the F functional group of the polyfunctionalized diene monomer-containing polymer comprises a cationic polymerizable functionalizing group. In certain embodiments of the first-fourth, the F functional group of the polyfunctionalized diene monomer-containing polymer comprises a combination of cationic polymerizable and free radical polymerizable functional groups either on the same diene polymer chain or on separate diene polymer chains. Generally, functional groups that are free radical polymerizable have the advantage of reacting faster than cationic polymerizable functionalizing groups, but the disadvantage is being prone to inhibition by oxygen exposure. Generally, functional groups that are cationic polymerizable have the advantage of being resistant to oxygen exposure (i.e., they are not inhibited), but have the disadvantages of being prone to inhibition by water exposure and having a generally slower rate of reaction. The combination of cationic polymerizable and free radical polymerizable functional groups can be advantageous as providing the advantages of each type and minimizing the disadvantages of each alone; an additional advantage of such a combination is to allow for a double network system wherein a crosslink of a first type occurs at a first wavelength and a crosslink of a second type occurs at a second wavelength or a single wavelength is used to activate both types of photoinitiators which will create a double network.

In certain embodiments of the first-fourth embodiments, each functional group F in the polyfunctionalized diene monomer-containing polymer at least one of: acrylate, methacrylate, cyanoacrylate, epoxide, aziridine, and thioepoxide. In certain embodiments of the first-fourth embodiments, each functional group F in the polyfunctionalized diene monomer-containing polymer comprises an acrylate or methacrylate. Suitable acrylates or methacrylates may be linear, branched, cyclic, or aromatic. As used herein, the term acrylate should be understood to include both acrylic acid and esters thereof. Similarly, the term methacrylate should be understood to include both methacrylic acid and esters thereof. Various types of acrylates and methacrylates are commonly used and may be suitable for use as the functional group F. In certain embodiments of the first-fourth embodiments disclosed herein, the function group F comprises at least one of: acrylic acid, methacrylic acid, ethyl (meth)acrylate, methyl (meth)acrylate, butyl (meth)acrylate, isobutyl (meth)acrylate, cyclobutyl (meth)acrylate, (cyano)acrylate, 2-ethylhexyl(meth)acrylate, isostearyl (meth)acrylate, isobornyl (meth)acrylate, propyl (meth)acrylate, isopropyl (meth)acrylate, cyclopropyl (meth)acrylate, pentyl (meth)acrylate, isopentyl (meth)acrylate, cyclopentyl (meth)acrylate, hexyl (meth)acrylate, isohexyl (meth)acrylate, cyclohexyl (meth)acrylate, heptyl (meth)acrylate, isoheptyl (meth)acrylate, cycloheptyl (meth)acrylate, octyl (meth)acrylate, cyclooctyl (meth)acrylate, nonyl (meth)acrylate, isononyl (meth)acrylate, cyclononyl (meth)acrylate, decyl (meth)acrylate, isodecyl (meth)acrylate, cyclodecyl (meth)acrylate, undecyl (meth)acrylate, isoundecyl (meth)acrylate, cycloundecyl (meth)acrylate, lauryl (meth)acrylate, tridecyl (meth)acrylate, isotridecyl (meth)acrylate, cyclotridecyl (meth)acrylate, tetradecyl (meth)acrylate, isotetradecyl (meth)acrylate, cyclotetradecyl (meth)acrylate, pentadecyl (meth)acrylate), isopentadecyl (meth)acrylate, cyclopentadecyl (meth)acrylate, and combinations thereof. In certain embodiments of the first-fourth embodiments, each functional group F in the polyfunctionalized diene monomer-containing polymer comprises an epoxide or a thioepoxide. In certain embodiments of the first-fourth embodiments, each functional group F in the polyfunctionalized diene monomer-containing polymer comprises an aziridine, which generally can be considered to be a compound containing the aziridine functional group (a 3-membered heterocyclic group with one amine (—NR—), where R is H, $CH_3$, and two methylenes (—$CH_2$—).

In certain embodiments of the first-fourth embodiments, the chain extender may be chosen based upon compound having a moiety that is reactive with the F functional group of the polyfunctionalized diene monomer-containing polymer.

In certain embodiments of the first-fourth embodiments, the chain extender comprises one or more additional functional groups F1 along the backbone of the polymer. Such functional groups may be chosen based upon their contribution to desirable properties in the cured polymeric mixture, the cured elastomeric 3-dimensional article or final product. As a non-limiting example, the F1 functional groups may be selected to interact with one or more fillers such as silica filler, i.e., F1 comprises a silica-reactive functional group. Thus, in certain embodiments of the first-fourth embodiments, the polyfunctionalized diene monomer-containing polymer comprises at least one F1 silica-reactive functional group along its backbone. Non-limiting examples of silica-reactive functional groups include nitrogen-containing functional groups, silicon-containing functional groups, oxygen- or sulfur-containing functional groups, and metal-containing functional groups. Another specific example of a F1 functional group includes phosphorous-containing functional groups.

Non-limiting examples of nitrogen-containing functional groups that can be utilized as a F1 silica-reactive functional group along the backbone of the polyfunctionalized diene monomer-containing polymer in certain embodiments include, but are not limited to, any of a substituted or unsubstituted amino group, an amide residue, an isocyanate group, an imidazolyl group, an indolyl group, a nitrile group, a pyridyl group, and a ketimine group. The foregoing substituted or unsubstituted amino group should be understood to include a primary alkylamine, a secondary alkylamine, or a cyclic amine, and an amino group derived from a substituted or unsubstituted imine. In certain embodiments of the first-third embodiments, the polyfunctionalized diene monomer-containing polymer comprises at least one F1 functional group along its backbone selected from the foregoing list of nitrogen-containing functional groups.

Non-limiting examples of silicon-containing functional groups that can be utilized as a F1 silica-reactive functional group along the backbone of the polyfunctionalized diene monomer-containing polymer in certain embodiments include, but are not limited to, an organic silyl or siloxy group, and more precisely, the functional group may be selected from an alkoxysilyl group, an alkylhalosilyl group, a siloxy group, an alkylaminosilyl group, and an alkoxyhalosilyl group. Suitable silicon-containing functional groups for use in functionalizing diene-based elastomer also include those disclosed in U.S. Pat. No. 6,369,167, the entire disclosure of which is herein incorporated by reference. In certain embodiments of the first-fourth embodiments, the polyfunctionalized diene monomer-containing polymer comprises at least one F1 functional group along its backbone selected from the foregoing list of silicon-containing functional groups.

Non-limiting examples of oxygen- or sulfur-containing functional groups that can be utilized as a F1 silica-reactive functional group along the backbone of the polyfunctionalized diene monomer-containing polymer in certain embodiments include, but are not limited to, a hydroxyl group, a carboxyl group, an epoxy group, a glycidoxy group, a diglycidylamino group, a cyclic dithiane-derived functional group, an ester group, an aldehyde group, an alkoxy group, a ketone group, a thiocarboxyl group, a thioepoxy group, a thioglycidoxy group, a thiodiglycidylamino group, a thioester group, a thioaldehyde group, a thioalkoxy group, and a thioketone group. In certain embodiments of the first-fourth, the foregoing alkoxy group may be an alcohol-derived alkoxy group derived from a benzophenone. In certain embodiments of the first-fourth embodiments, the polyfunctionalized diene monomer-containing polymer comprises at least one F1 functional group along its backbone selected from the foregoing list of oxygen- or sulfur-containing functional groups.

Non-limiting examples of phosphorous-containing functional groups that can be utilized as a F1 functional group along the backbone of the polyfunctionalized diene monomer-containing polymer in certain embodiments include, but are not limited to, organophosphorous compounds (i.e., compounds containing carbon-phosphorous bond(s)) as well as phosphate esters and amides and phosphonates. Non-limiting examples of organophosphorous compounds include phosphines including alkyl phosphines and aryl phosphines. In certain embodiments of the first-fourth embodiments, the polyfunctionalized diene monomer-containing polymer comprises at least one F1 functional group along its backbone selected from the foregoing list of phosphorous-containing functional groups.

Chain Extender

As discussed above, the actinic radiation curable polymeric mixture optionally comprises a chain extender based upon F or reactive with F. In other words, in certain embodiments of the first-fourth embodiments, the mixture comprises a chain extender, but it is not considered to be essential in all embodiments. Generally, the chain extender is a hydrocarbon or hydrocarbon derivative that is monofunctionalized with a functional group that reacts with a functional end group of the diene polymer chain of the polyfunctionalized diene monomer-containing polymer and is used to increase the molecular weight of the polyfunctionalized diene monomer-containing polymer (by bonding to one of the F groups of the polymer). Preferably, the chain extender lowers the viscosity of the overall actinic radiation curable polymeric mixture and also acts to increase the molecular weight of the polyfunctionalized diene monomer-containing polymer between crosslinks. In certain embodiments of the first-fourth embodiments, the chain extender also increases the elongation at break of the cured elastomeric/polymeric mixture that results from actinic radiation curing the polymeric mixture.

In certain embodiments of the first-fourth embodiments when the chain extender is present, it comprises a compound that is based upon F. In other words, such a chain extender compound comprises an F group. In certain embodiments of the first-fourth embodiments when the chain extender is present, it comprises a compound that is based upon F or a compound that is reactive with F. By reactive with F is meant a compound containing a moiety that will bond with the F group of the polyfunctionalized diene monomer-containing polymer.

As discussed above, in those embodiments of the first-fourth embodiments where the chain extender is present, it may comprise a hydrocarbon or hydrocarbon derivative with monofunctionality selected from various functional groups either based on F or reactive with F. In certain embodiments when the chain extender is present, it is selected so that the Tg of the chain-extended polyfunctionalized diene monomer-containing polymer is less than about 25° C., including about −65° C. to about 10° C. Preferably, the chain extender is selected so that the Tg of the extended polyfunctionalized diene monomer-containing polymer even after crosslinking is less than about 25° C., including about −65° C. to about 10° C. In certain embodiments of the first-fourth embodiments, when the chain extender is present, it comprises a compound that has a Mw of about 72 to about 1000 grams/mole, including about 72 to about 500 grams/mole.

In certain embodiments of the first-fourth embodiments, when the chain extender is present, it comprises at least one alkyl (meth)acrylate monomer. In certain such embodiments, the alky (meth)acrylate monomer is comprised of an alkyl chain selected from C2 to about C18 and having a reactive meth(acrylate) head group, termed alkyl functionalized (meth)acrylates; alkyl (meth)acrylate monomers having larger alkyl groups may have a thermal transition, Tm, that is higher than desired. By utilizing as a chain extender a compound/monomer that contains only one functional group (e.g., a (meth)acrylate) it is possible to increase the molecular weight between crosslinks, while reducing the viscosity.

In certain embodiments of the first-fourth embodiments, when the F group of the polyfunctionalized diene monomer-containing polymer comprises an acrylate or methacrylate, the chain extender comprises at least one alkyl (meth)acrylate monomer. In certain such embodiments, the alky (meth)acrylate monomer is at least one monomer selected from C2 to about C18 alkyl functionalized (meth)acrylates;

alkyl (meth)acrylate monomers having larger alkyl groups may have a Tg that is higher than desired and may unduly increase the Tg of the overall actinic radiation curable polymeric mixture.

In certain embodiments of the first-fourth embodiments, the total amount of polyfunctionalized diene monomer-containing polymer and chain extender can be considered to be 100 parts by weight; in certain such embodiments, the polyfunctionalized diene monomer-containing polymer is present in an amount of 1-100 parts by weight and the chain extender is present in an amount of 0-99 parts by weight. In other words, the chain extender is optional in certain embodiments. Generally, the relative amounts of polyfunctionalized diene monomer-containing polymer and chain extender can vary greatly because, as discussed above, upon exposure to actinic radiation the chain extender adds to the polymer and increases its molecular weight. As a non-limiting example, when the Mn of the polyfunctionalized diene monomer-containing polymer is relatively low (e.g., about 3,000 grams/mole, polystyrene standard), and the Mw of the chain extender is relatively high (e.g., about 1000 grams/mole), the total amount of polyfunctionalized diene monomer-containing polymer and chain extender can comprise relatively less polymer than chain extender. In certain embodiments of the first-fourth embodiments, the polyfunctionalized diene monomer-containing polymer is present in an amount of 1-90 parts by weight and the chain extender is present in an amount of 10-99 parts by weight, including 1-80 parts by weight polyfunctionalized diene monomer-containing polymer and the chain extender is present in an amount of 20-99 parts by weight, 1-70 parts by weight polyfunctionalized diene monomer-containing polymer and the chain extender is present in an amount of 30-99 parts by weight, 1-60 parts by weight polyfunctionalized diene monomer-containing polymer and the chain extender is present in an amount of 40-99 parts by weight, 1-50 parts by weight polyfunctionalized diene monomer-containing polymer and the chain extender is present in an amount of 50-99 parts by weight, 1-40 parts by weight polyfunctionalized diene monomer-containing polymer and the chain extender is present in an amount of 60-99 parts by weight, 1-30 parts by weight polyfunctionalized diene monomer-containing polymer and the chain extender is present in an amount of 70-99 parts by weight, 1-20 parts by weight polyfunctionalized diene monomer-containing polymer and the chain extender is present in an amount of 80-99 parts by weight, 1-10 parts by weight polyfunctionalized diene monomer-containing polymer and the chain extender is present in an amount of 10-99 parts by weight. In certain embodiments of the first-fourth embodiments, the polyfunctionalized diene monomer-containing polymer is present in an amount of 10-99 parts by weight and the chain extender is present in an amount of 1-90 parts by weight, including 20-99 parts by weight polyfunctionalized diene monomer-containing polymer and the chain extender is present in an amount of 1-80 parts by weight, 30-99 parts by weight polyfunctionalized diene monomer-containing polymer and the chain extender is present in an amount of 1-70 parts by weight, 40-99 parts by weight polyfunctionalized diene monomer-containing polymer and the chain extender is present in an amount of 1-60 parts by weight, 50-99 parts by weight polyfunctionalized diene monomer-containing polymer and the chain extender is present in an amount of 1-50 parts by weight, 60-99 parts by weight polyfunctionalized diene monomer-containing polymer and the chain extender is present in an amount of 1-40 parts by weight, 70-99 parts by weight polyfunctionalized diene monomer-containing polymer and the chain extender is present in an amount of 1-30 parts by weight, 80-99 parts by weight polyfunctionalized diene monomer-containing polymer and the chain extender is present in an amount of 1-20 parts by weight, 90-99 parts by weight polyfunctionalized diene monomer-containing polymer and the chain extender is present in an amount of 1-10 parts by weight.

In certain embodiments of the first-fourth embodiments, when the F groups of the polyfunctionalized diene monomer-containing polymer comprise (meth)acrylate and the F groups of the chain extender comprise an alkyl (meth)acrylate, the relative amounts of polymer and chain extender are about 50 parts and 50 parts, respectively, including about 40 to about 60 parts polymer and about 60 to about 40 parts chain extender; 40 to 60 parts polymer and 60 to 40 parts chain extender; about 45 to about 60 parts polymer and about 55 to about 40 parts chain extender; 45 to 60 parts polymer and 55 to 40 parts chain extender; about 50 to about 60 parts polymer and about 40 to about 50 parts chain extender; 50 to 60 parts polymer and 40 to 50 parts chain extender; about 55 to about 60 parts polymer and about 40 to about 45 parts chain extender; and 55 to 60 parts polymer and 40 to 45 parts chain extender.

In certain embodiments of the first-fourth embodiments, in addition to being monofunctionalized with at least one F group or a functional group reactive with F, the chain extender is further functionalized with at least one functional group F2 that is molecular oxygen reactive. Non-limiting examples of suitable F2 groups include various amines, including, but not limited to, tertiary amines, secondary amines, and primary amines; thiols; silanes; phosphites, tin-containing compounds, lead containing compounds, and germanium-containing compounds. Incorporating at least one molecular oxygen reactive F2 functional group into the chain extender reduces the amount of undesirable oxidation that may otherwise occur from either solubilized oxygen within the actinic radiation curable polymeric mixture or atmospheric oxygen. Without being bound by theory, a functional group F2 that is molecular oxygen reactive can react with any peroxy radicals that are generated (e.g., from the reaction of a free radical with molecular oxygen) to create a new initiator by hydrogen absorption; this reaction avoids or minimizes the undesirable reaction between a peroxy radical and an initiator (which will yield a non-productive product and consume the initiator). The amount of F2 functionalization on the chain extender may vary. In certain embodiments of the first-fourth embodiments, the chain extender is about 10 to 100% functionalized with at least one functional group F2 that is molecular oxygen reactive, including 10 to 100% functionalized, about 20 to 100% functionalized, 20 to 100% functionalized, about 30 to 100% functionalized, 30 to 100% functionalized, about 40 to 100% functionalized, 40 to 100% functionalized, about 50 to 100% functionalized, 50 to 100% functionalized, about 10 to about 90% functionalized, 10 to 90% functionalized, about 10 to about 80% functionalized, 10 to 80% functionalized, about 10 to about 70% functionalized, 10 to 70% functionalized, about 10 to about 60% functionalized, 10 to 60% functionalized, about 10 to about 50% functionalized, and 10 to 50% functionalized. In other embodiments, in addition to comprising at least one functional group F2 that is molecular oxygen reactive or as an alternative to comprising at least one functional group F2 that is molecular oxygen reactive, a separate molecular oxygen reactive ingredient can be utilized in the actinic radiation curable polymeric mixture. Generally, this separate ingredient comprises a hydrocarbon or hydrocarbon derivative functionalized with at least one of the functional groups discussed above for F2.

Photoinitiator

As discussed above, the actinic radiation curable polymeric mixture comprises at least one actinic radiation sensitive photoinitiator. In certain embodiments of the first-fourth embodiments, the polymeric mixture comprises two, three, or more one actinic radiation sensitive photoinitiators. Generally, the purpose of the photoinitiator is to absorb actinic radiation (light) and generate free radicals or a Lewis acid that will react with the functional groups of the polymer resulting in polymerization. Two types of actinic radiation sensitive photoinitiators exist: free radical and cationic. Free radical photoinitiators can themselves be separated into two categories, those that undergo cleavage upon irradiation to generate two free radicals (e.g., benzoins, benzoin ethers, and alpha-hydroxy ketones) and those that form an excited state upon irradiation and then abstract an atom or electron from a donor molecule which itself then acts as the initiating species for polymerization (e.g., benzophenones). In certain embodiments of the first-fourth embodiments disclosed herein, the photoinitiator comprises at least one free radical photoinitiator. In certain embodiments of the first-fourth embodiments disclosed herein, the photoinitiator comprises at least one cationic photoinitiator. In certain embodiments of the first-fourth embodiments disclosed herein, the photoinitiator comprises a combination of at least one free radical photoinitiator and at least one cationic photoinitiator.

When a photoinitiator is utilized, various photoinitiators are suitable for use in the actinic radiation curable polymeric mixtures. In certain embodiments of the first-fourth embodiments disclosed herein, the photoinitiator comprises at least one of: a benzoin, an aryl ketone, an alpha-amino ketone, a mono- or bis(acyl)phosphine oxide, a benzoin alkyl ether, a benzil ketal, a phenylglyoxalic ester or derivatives thereof, an oxime ester, a per-ester, a ketosulfone, a phenylglyoxylate, a borate, and a metallocene. In certain embodiments of the first-fourth embodiments disclosed herein, the photoinitiator comprises at least one of: a benzophenone, an aromatic α-hydroxyketone, a benzilketal, an aromatic α-aminoketone, a phenylglyoxalic acid ester, a mono-acylphosphinoxide, a bis-acylphosphinoxide, and a tris-acylphosphinoxide. In certain embodiments of the first-fourth embodiments disclosed herein, the photoinitiator is selected from benzophenone, benzildimethylketal, 1-hydroxy-cyclohexyl-phenyl-ketone, 1-[4-(2-hydroxyethoxy)-phenyl]-2-hydroxy-2-methyl-1-propan-1one, 2-hydroxy-1-{4-[4-(2-hydroxy-2-methyl-propionyl)-benzyl]-phenyl}-2-methyl-propan-1-one, (4-methylthiobenzoyl)-1-methyl-1-morpholinoethane, (4-morpholinobenzoyl)-1-benzyl-1-dimethylaminopropane, (4-morpholinobenzoyl)-1-(4-methylbenzyl)-1-dimethylaminopropane, (2,4,6-trimethylbenzoyl)diphenylphosphine oxide, bis(2,6-dimethoxy-benzoyl)-(2,4,4-trimethyl-pentyl) phosphine oxide, bis(2,4,6-trimethylbenzoyl)-phenylphosphine oxide and 2-hydroxy-1-{1-[4-(2-hydroxy-2-methyl-propionyl)-phenyl]-1,3,3-trimethyl-indan-5-yl}-2-methyl-propan-1-one, 1,2-octanedione, 1-[4-(phenylthio)phenyl]-2-(O-benzyloxime), oligo[2-hydroxy-2-methyl-1-[4-methylvinyl]phenyl]propanone, 2-hydroxy-2-methyl-1-phenyl propan-1-one, and combinations thereof.

The amount of actinic radiation sensitive photoinitiator(s) utilized can vary. In certain embodiments of the first-fourth embodiments disclosed herein, when the photoinitiator is present, the actinic radiation curable polymeric mixture comprises about 1 to about 10 parts by weight of the photoinitiator, including about 2 to about 5 parts by weight (all amounts based upon 100 total parts of polyfunctionalized diene monomer-containing polymer and chain extender). The foregoing amounts should be understood to apply to both free radical and cationic photoinitiators and to refer to the total amounts (by weight) of all photoinitiators used in the actinic radiation curable polymeric mixture.

Photosensitizer

As discussed above, in certain embodiments of the first-fourth embodiments, the actinic radiation curable polymeric mixture comprises a photosensitizer. In other words, in certain embodiments of the first-fourth embodiments, the photosensitizer is optional. Generally, the "photosensitizer" is a light absorbing compound used to enhance the reaction of a photoinitiator; it may absorb part of the actinic radiation (light) that the photoinitiator cannot absorb and transfer the energy to the photoinitiator. Upon photoexcitation, a photosensitizer leads to energy or electron transfer to a photoinitiator.

In those embodiments of the first-fourth embodiments where a photosensitizer is used, the amount of photosensitizer utilized can vary. (As discussed above, the photosensitizer is not necessarily present in every embodiment disclosed herein.) In certain embodiments of the first-fourth embodiments disclosed herein, when the photosensitizer is present, the actinic radiation curable polymeric mixture comprises about 0.1 to about 5 parts by weight of the photosensitizer, including about 0.1 to about 2 parts by weight (all amounts based upon 100 total parts of polyfunctionalized diene monomer-containing polymer and chain extender).

When a photosensitizer is utilized, various photosensitizers are suitable for use in the actinic radiation curable polymeric mixtures. In certain embodiments of the first-fourth embodiments disclosed herein, the photosensitizer comprises at least one of a ketocoumarin, a xanthone, a thioxanthone, a polycyclic aromatic hydrocarbon, and an oximester derived from aromatic ketone. Exemplary ketocoumarins are disclosed in Tetrahedron 38, 1203 (1982), and U.K. Patent Publication 2,083,832 (Specht et al.).

Crosslinker

As discussed above, the actinic radiation curable mixture comprises a polyfunctional crosslinker reactive with the functional group F of the polyfunctionalized diene monomer-containing polymer. Generally, the polyfunctional crosslinker functions to increase the amount of crosslinking within each diene polymer chain of the polyfunctionalized diene monomer-containing polymer, between (separate) diene polymer chains of polyfunctionalized diene monomer-containing polymers, or both, thereby forming a network. Generally, an increased amount of crosslinker or crosslinking will lower the Mc of the crosslinked (cured) polyfunctionalized diene monomer-containing polymer, thereby resulting in a higher modulus and a lower Eb. In certain embodiments of the first-fourth embodiments, the polyfunctional crosslinker is a hydrocarbon or hydrocarbon derivative polyfunctionalized with a functional group F. In other words, such a crosslinker comprises multiple F groups. In certain embodiments of the first-fourth embodiments, the crosslinker is a hydrocarbon or hydrocarbon derivative polyfunctionalized with a functional group F or a functional group that is reactive with F. By reactive is meant a moiety that will bond with at least two F groups of the polyfunctionalized diene monomer-containing polymer.

Generally, the crosslinker is a polyfunctionalized hydrocarbon or hydrocarbon derivative containing at least two functional groups reactive with F. In certain embodiments of the first-fourth embodiments, the crosslinker is di-functional and in other embodiments, the crosslinker is tri-functional, tetra-functional, or further functionalized. While the crosslinker is based upon a hydrocarbon or hydrocarbon derivative, it should be understood that it can also be polymer-like in that it can comprise either a single base unit or multiple, repeating base units.

Various compounds are suitable for use as the crosslinker. In certain embodiments of the first-fourth embodiments, the crosslinker contains at least two (meth)acrylate functional groups. In certain embodiments of the first-fourth embodiments, the crosslinker comprises a polyol (meth)acrylate prepared from an aliphatic diol, triol, or tetraol containing 2-100 carbon atoms; in such embodiments, the functional group of the crosslinker is (meth)acrylate. Various crosslinkers comprising at least two (meth)acrylate groups are commercially available. In certain embodiments of the first-fourth embodiments, the crosslinker comprises at least one of the following: Trimethylolpropane tri(meth)acrylate, Pentaerythritol tetraacrylate, Pentaerythritol triacrylate, Trimethylolpropane ethoxylate triacrylate, Acrylated epoxidized soybean oil, Ditrimethylol Propane Tetraacrylate, Di-pentaerythritol Polyacrylate, Di-pentaerythritol Polymethacrylate, Di-pentaerythritol triacrylate, Di-pentaerythritol trimethacrylate, Di-pentaerythritol tetraacrylate, Di-pentaerythritol tetramethacrylate, Di-pentaerythritol pent(meth)acrylate, Di-pentaerythritol hexa(meth)acrylate, Pentaerythritol Poly(meth)acrylate, Pentaerythritol tri(meth)acrylate, Pentaerythritol tetra(meth)acrylate, Pentaerythritol penta(meth)acrylate, Pentaerythritol hexa(meth)acrylate, Ethoxylated glycerine triacrylate, ε-Caprolactone ethoxylated isocyanuric acid triacrylate and Ethoxylated isocyanuric acid triacrylate, Tris(2-acryloxyethyl) Isocyanulate, Propoxylated glyceryl Triacrylate, ethyleneglycol diacrylate, 1,6-hexanediol diacrylate, neopentylglycol di(meth)acrylate, ethyleneglycol dimethacrylate (EDMA), polyethyleneglycol di(meth)acrylates, polypropyleneglycol di(meth)acrylates, polybutyleneglycol di(meth)acrylates, 2,2-bis(4-(meth)acryloxyethoxyphenyl) propane, 2,2-bis(4-(meth)acryloxydiethoxyphenyl) propane, di(trimethylolpropane) tetra(meth)acrylate, and combinations thereof.

In certain embodiments of the first-fourth embodiments, the crosslinker comprises a polyallylic compound prepared from an aliphatic diol, triol or tetraol containing 2-100 carbon atoms. Exemplary polyallylic compounds useful as crosslinker include those compounds comprising two or more allylic groups, non-limiting examples of which include triallylisocyanurate (TAIC), triallylcyanurate (TAC), and the like, and combinations thereof.

In certain embodiments of the first-fourth embodiments, the crosslinker comprises epoxy functional groups, aziridine functional groups, vinyl functional groups, allyl functional groups, or combinations thereof.

In certain embodiments of the first-fourth embodiments, the crosslinker comprises a polyfunctional amine with at least two amine groups per molecule. In certain such embodiments, the polyfunctional amine is an aliphatic amine. Exemplary polyfunctional amines include, but are not limited to, diethylene triamine, ethylene diamine, triethylene tetramine, tetraethylene pentamine, hexamethylerie diamine, 1,2-diaminocyclohexane, amino ethyl piperazine, and the like, and combinations thereof.

In certain embodiments of the first-fourth embodiments, the polyfunctional crosslinker comprises a combination of two types of functional groups, i.e., a functional group capable of crosslinking at least two diene polymer chains based upon cationic radiation and a functional group capable of crosslinking at least two diene polymer chains based upon free radical radiation. The combination of two types of functional groups may be present on the same polyfunctional crosslinker or on separate crosslinkers (i.e., each with one type of functional group). In certain embodiments of the first-fourth, the polyfunctional crosslinker comprises a combination of at least one functional group selected from acrylate groups, methacrylate groups, polyallylic groups, and polyfunctional amines with at least one functional group selected from epoxy groups, aziridine groups, vinyl groups, and allyl groups.

Resins

As mentioned above, in certain embodiments of the first-fourth embodiments, the curable polymeric mixture of the liquid binder further comprises (includes) at least one resin; in certain such embodiments the at least one resin comprises at least one of: UV curable resin, IR curable resin, or heat curable resin. In certain embodiments of the first-fourth embodiments, the curable polymeric mixture of the liquid binder comprises at least one UV curable resin. According to the first-fourth embodiments, the particular UV curable resin used in the curable polymeric mixture may vary. In certain embodiments of the first-fourth embodiments, the UV curable resin cures via a free radical reaction. Non-limiting examples of such resins include acrylates and methacrylates, and combinations of one or more of the foregoing may also be utilized. In certain embodiments of the first-fourth embodiments, the UV curable resin cures via a cationic reaction. Non-limiting examples of such resins include epoxies, including but not limited to, cycloaliphatic epoxies, and combinations of one or more of the foregoing may also be utilized.

In certain embodiments of the first-fourth embodiments, the curable polymeric mixture comprises at least one IR curable resin. According to the first-fourth embodiments, the particular IR curable resin used in the curable polymeric mixture may vary. Non-limiting examples of such resins include epoxies, urethanes, and phenol-formaldehydes, and combinations of one or more of the foregoing may also be utilized. In addition, it should be understood that certain resins which are heat curable can also be considered to be IR curable.

In certain embodiments of the first-fourth embodiments, the curable polymeric mixture comprises at least one heat curable resin. Non-limiting examples of such resins include epoxies, urethanes and phenol-formaldehydes, and combinations of one or more of the foregoing may also be utilized.

In certain embodiments of the first-fourth embodiments, the curable polymeric mixture comprises at least one of the following types of resins: (1) phenolic resins such as phenol novolak resins, phenol-formaldehyde resins, resorcinol-formaldehyde resins, reactive resol resins (which can react with unsaturation in an elastomer or rubber to contribute to crosslinking), and reactive novolak type phenol-formaldehyde resins (which can crosslink with methylene donors); (2) aliphatic resins such as such as C5 fraction homopolymer or copolymer resins, optionally in combination with one or more of e.g., cycloaliphatic, aromatic, hydrogenated aromatic, or terpene resins and/or optionally partially or fully hydrogenated; (3) cycloaliphatic resins (such as cyclopentadiene ("CPD") homopolymer or copolymer resins, and dicyclopentadiene ("DCPD") homopolymer or copolymer resins), optionally in combination with one or more of aliphatic, aromatic, hydrogenated aromatic, or terpene resins, and/or optionally partially or fully hydrogenated; (4) aromatic resins (such as coumarone-indene resins and alkyl-phenol resins as well as vinyl aromatic homopolymer or copolymer resins such as those including one or more of the following monomers: alpha-methylstyrene, styrene, orthomethylstyrene, meta-methylstyrene, para-methylstyrene, vinyltoluene, para(tert-butyl)styrene, methoxystyrene, chlorostyrene, hydroxystyrene, vinylmesitylene, divinylbenzene, vinylnaphthalene or any vinyl aromatic monomer resulting from C9 fraction or C8-C10 fraction), optionally in combination with one or more of aliphatic, cycloaliphatic, hydrogenated aromatic, or terpene resins, and/or optionally partially or fully hydrogenated; (5) terpene resins (such as alpha-pinene resins, beta-pinene resins, limonene resins (e.g., L-limonene, D-limonene, dipentene which is a racemic mixture of L- and D-isomers), beta-phellandrene, delta-3-carene, and delta-2-carene), optionally in combination with one or more of aliphatic, cycloaliphatic, aromatic, or hydrogenated aromatic resins, and/or optionally partially or fully hydrogenated; (6) rosin resins (such as gum rosin, wood rosin, and tall oil rosin, glycerin ester rosins, and pentaerythritol ester rosins (optionally partially hydrogenated and/or polymerized)), optionally in combination with one or more of aliphatic, cycloaliphatic, aromatic, hydrogenated aromatic, or terpene resins, and/or optionally partially or fully hydrogenated; or (7) guayule resins. In certain embodiments of the first-fourth embodiments, more than one of a particular type of the foregoing resins is utilized and in other embodiments more than one each of at least two particular types of the foregoing resins is utilized. In certain embodiments of the first-fourth embodiments, the curable polymeric mixture comprises an unsaturated resin.

As discussed above, in certain embodiments of the first-fourth embodiments, the liquid binder comprises a cure package. According to those embodiments, the ingredients of the cure package may vary. In certain embodiments of the first-fourth embodiments, the cure package comprises a vulcanizing agent and at least one vulcanization accelerator. The amount and identity of the vulcanizing agent and at least one vulcanization accelerator may vary. In certain embodiments of the first-fourth embodiments, the cure package further comprises (includes) in addition to the vulcanizing agent and at least one accelerator, at least one of: a vulcanizing activator (e.g., zinc oxide, stearic acid, and the like); a vulcanizing inhibitor; and an anti-scorching agent. In certain embodiments of the first-fourth embodiments, the cure package includes at least one vulcanizing agent, at least one vulcanization accelerator, at least one vulcanizing activator, and optionally a vulcanizing inhibitor and/or an anti-scorching agent. Vulcanizing accelerators and vulcanizing activators act as catalysts for the vulcanization agent. Vulcanizing inhibitors and anti-scorching agents are known in the art and can be selected by one skilled in the art based on the vulcanizate properties desired.

In certain embodiments of the first-fourth embodiments, the vulcanizing agent of the cure package of the liquid binder comprises sulfur or peroxide-based curing components. Thus, in certain such embodiments of the first-fourth embodiments, the cure package includes a sulfur-based vulcanizing agent or a peroxide-based vulcanizing agent. Examples of specific suitable sulfur vulcanizing agents include "rubbermaker's" soluble sulfur; sulfur donating curing agents, such as an amine disulfide, polymeric polysulfide, or sulfur olefin adducts; and insoluble polymeric sulfur. In certain embodiments of the first-fourth embodiments, the sulfur vulcanizing agent is soluble sulfur or a mixture of soluble and insoluble polymeric sulfur. For a general disclosure of suitable vulcanizing agents and other components used in curing, e.g., vulcanizing inhibitor and anti-scorching agents, one can refer to Kirk-Othmer, Encyclopedia of Chemical Technology, 3rd ed., Wiley Interscience, N.Y. 1982, Vol. 20, pp. 365 to 468, particularly Vulcanization Agents and Auxiliary Materials, pp. 390 to 402, or Vulcanization by A. Y. Coran, Encyclopedia of Polymer Science and Engineering, Second Edition (1989 John Wiley & Sons, Inc.), both of which are incorporated herein by reference. Vulcanizing agents can be used in the liquid binder alone or in combination. Generally, when present, the vulcanizing agents are used in a total amount ranging from 0.1 to 10 phr, including from 1 to 7.5 phr, including from 1 to 5 phr, and preferably from 1 to 3.5 phr (with the phr being based upon 100 parts of rubber or polymer in the liquid binder).

In certain embodiments of the first-fourth embodiments disclosed herein, the at least one vulcanization accelerator is selected from at least one of the following classes of vulcanization accelerators: thiurams, thioureas, dithiocarbamates, xanthates, thiophosphates, thiazoles, guanidines, or carbamates. Non-limiting examples of vulcanizing accelerators that belong to the class of thiurams include: TMTM (tetramethyl thiuram monosulfide), TMTD (tetramethyl thiuram disulfide), DPTT (dipentamethylene thiuram tetrasulfide), TETD (tetraethyl thiuram disulfide), TiBTD (tetraisobutyl thiuram disulfide), and TBzTD (tetrabenzyl thiuram disulfide). Non-limiting examples of vulcanizing accelerators that belong to the class of thioureas include: ETU (ethylene thiourea), DPTU (N,N-diethyl thiourea), DETU (N,N-dibutylthiourea), and DBTU (diphenyl thiourea). Non-limiting examples of vulcanizing accelerators that belong to the class of dithiocarbamates include: ZDMC (zinc dimethyl dithiocarbamate), ZDEC (zinc diethyl dithiocarbamate), ZDBC (zinc dibutyl dithiocarbamate), ZEDC (zinc N-ethyl-dithiocarbamate), CDMC (copper dimethyl dithiocarbamate) and ZBEC (zinc dibenzyl dithiocarbamate). Non-limiting examples of vulcanizing accelerators that belong to the class of xanthates include: ZIX (zinc isopropyl xanthate). Non-limiting examples of vulcanizing accelerators that belong to the class of thiophosphates include: ZBDP (Zinc-O,O-di-N-phosphorodithioate). Non-limiting examples of vulcanizing accelerators that belong to the class of thiazoles include: MBT (2-mercaptobenzothiazole), MBTS (2,2-benzothiazole disulfide), ZMBT (zinc 2-mercaptobenzothiazole) and CMBT (copper 2-mercaptobenzothiazole). Non-limiting examples of vulcanizing accelerators that belong to the class of sulfenamides include: N-cyclohexyl-2-benzothiazole-sulfenamide (CBS), N-tert-butyl-2-benzothiazole-sulfenamide (TBBS), and the like. Non-limiting examples of vulcanizing accelerators that belong to the class of guanidines include: diphenyl guanidine (DPG), N,N'-di-ortho-tolyl guanidine (DOTG) and the like. Non-limiting examples of vulcanizing accelerators that belong to the class of carbamates include: zinc dibutyl dithiocarbamate (ZDBC), zinc dibenzyl dithiocarbamate (ZBEC), zinc diethyl dithiocarbamate (ZDEC), zinc dimethyl dithiocarbamate (ZDMC), zinc N-ethyl-dithiocarbamate (ZEDC), copper dimethyl dithiocarbamate (CDMC), and the like). The foregoing vulcanization accelerators can be used either from one class (alone, in combination with other accelerators from that class), or from more than one class. Generally, the total amount of vulcanization accelerator (when used) ranges from 0.5 to 15 phr (e.g., 0.5, 1, 2, 3, 4, 5, 6, 7, 8, 9, 10, 11, 12, 13, 14, 15 phr), 0.5 to 10 phr, 1 to 5 phr, or 2 to 10 phr. In certain embodiments of the first-fourth embodiments, the vulcanizing agent (when present) is used in an amount ranging from 0.1 to 10 phr (e.g., 0.1, 0.5, 1, 2, 3, 4, 5, 6, 7, 8, 9, 10 phr), including from 0.1 to 7.5 phr, including from 0.1 to 5 phr, and preferably from 0.1 to 3.5 phr (with the phr being based upon 100 parts of rubber or polymer in the liquid binder).

Vulcanizing activators are additives used to support vulcanization. Generally vulcanizing activators include both an inorganic and organic component. Zinc oxide is the most widely used inorganic vulcanization activator. Various organic vulcanization activators are commonly used including stearic acid, palmitic acid, lauric acid, and zinc salts of each of the foregoing. In certain embodiments of the first-fourth embodiments, the cure package of the liquid binder includes a vulcanization activator in an amount of 0.1 to 6 phr, preferably 0.5 to 4 phr (with the phr being based upon 100 parts of rubber or polymer in the liquid binder).

Vulcanization inhibitors are used to control the vulcanization process and generally retard or inhibit vulcanization until the desired time and/or temperature is reached. Common vulcanization inhibitors include, but are not limited to, PVI (cyclohexylthiophthalmide) from Santogard. In certain embodiments of the first-fourth embodiments, the cure package of the liquid binder includes a vulcanization inhibitor in an amount of 0.1 to 3 phr, preferably 0.5 to 2 phr (with the phr being based upon 100 parts of rubber or polymer in the liquid binder).

Applying Liquid Binder to Form a First Bound Layer

As discussed above, the processes of the first-fourth embodiments comprise (include) applying of liquid binder to the rubber layers (i.e., the first rubber layer as well as at least some of the additional rubber layers), resulting in bound layers. Application of liquid binder to a given rubber layer results in a bound layer (e.g., application of liquid binder to the first rubber layer results in a first bound layer, application of liquid binder to a second rubber layer can be understood as resulting in a second bound layer, etc.). While application of liquid binder to the first rubber layer will generally be necessary to achieve a first bound layer, it should be understood that in certain embodiments of the first-fourth embodiments, separate application of liquid binder to each additional rubber layer may not be necessary to achieve subsequent bound layers. More specifically, a separate application of liquid binder to at least some of the additional rubber layers may be omitted under certain circumstances such as when a particular additional rubber layer is particularly thin, when the prior application of liquid binder has resulted in sufficient binder to allow for some of the binder to bind the next rubber layer, and/or when the curing of the prior bound layer has been incomplete and allowed for passage (or bleeding) of binder between layers (e.g., from a cured bound layer to the overlying rubber layer of rubber particles).

According to the processes of the first-fourth embodiments, the relative amount of liquid binder that is applied to a particular rubber layer to form a bound layer may vary. In certain embodiments of the first-fourth embodiments, the weight ratio of rubber particles to liquid binder in the first bound layer and any additional bound layers is 25/75 to 99/1 (e.g., 30/70, 35/65, 40/60, 45/55, 50/50, 55/45, 60/40, 65/35, 70/30, 75/25, 80/20, 85/15, 90/10, 95/5, 96/4, 97/3, or 98/2). In certain embodiments of the first-fourth embodiments, the weight ratio of rubber particles to liquid binder in the first bound layer and any additional bound layers is 40/60 to 80/20. In certain embodiments of the first-fourth embodiments, the weight ratio of rubber particles to liquid binder in the first bound layer and any subsequent bound layers is at least 51/49, i.e., the rubber particles represent a weight majority of the total weight of the bound layer. The relative amount of liquid binder that is applied to a particular rubber layer to form a bound layer and, hence, the weight ratio of rubber particles to liquid binder may vary from one bound layer to another. Alternatively, the relative amount of liquid binder that is applied to a particular rubber layer to form a bound layer and, hence, the weight ratio of rubber particles to liquid binder may be the same or substantially the same (i.e., with 5 weight %) from one bound layer to another within the same cured polymeric product.

In certain embodiments, the processes of the first-fourth embodiments are modified such that the rubber particles are mixed with liquid binder prior to being formed into a first rubber layer or into additional rubber layers. In such embodiments, the mixing or coating of the rubber particles with liquid binder prior to forming of the rubber layers can reduce or even eliminate the need for applying liquid binder to the rubber layers to form bound layers. In certain such embodiments, the amount of liquid binder used in the step of applying liquid binder to the rubber layer to form bound layers is 50% or less of the amounts disclosed elsewhere herein (i.e., in those embodiments wherein the liquid binder is not pre-mixed or coated upon the rubber particles prior to forming of the rubber layer). Mixing or coating of the rubber particles with liquid binder may take place according to various processes including, but not limited to, mechanical milling, hot melting, solution phase coating, and combinations thereof. According to such modified processes, the curing may take place according to the processes described herein (i.e., by applying actinic radiation, heat or a combination thereof) to one or more of the layers containing the rubber particles mixed or coated with liquid binder. Thus, modified processes of the first-fourth embodiments wherein the rubber particles are mixed with liquid binder prior to being formed into a first rubber layer or additional rubber layers should be considered to be fully disclosed herein, including with the various combinations and permutations disclosed for the processes of the first-fourth embodiments (e.g., details concerning rubber particles, details concerning binder ingredients, and details concerning effecting curing).

Effecting Curing

As discussed above, the processes of the first-fourth embodiments include a step of effecting curing by applying actinic radiation, heat, or a combination thereof to one or more of the bound layers. Generally, the application of actinic radiation, heat, or a combination thereof to one or more of the bound layers will occur after formation of a given bound layer but prior to formation of the next rubber layer upon the surface of that bound layer. By stating that actinic radiation, heat, or a combination thereof is applied to one or more of the bound layers is meant that each successive bound layer does not necessarily have a separate or successive application of actinic radiation, heat, or a combination thereof. In other words, in such embodiments, after formation of certain of the bound layers, an additional rubber layer is formed upon that bound layer without an intervening application of actinic radiation, heat, or a combination thereof. In other embodiments, curing is effected by applying actinic radiation, heat, or a combination thereof to each bound layer prior to formation of an additional rubber layer upon the surface of that bound layer.

In certain embodiments of the processes of the first-fourth embodiments, the applying of actinic radiation (i.e., to the first bound layer and/or to the additional bound layers) comprises selective application of actinic radiation to less than the entire bound layer. By stating that the actinic radiation is applied selectively to less than the entire bound layer is meant that the actinic radiation is not necessarily applied to the entire surface of the bound layer. Such selective application allows for curing of only portions of the respective bound layer, thereby facilitating formation of certain structures such as voids or negative spaces. In certain embodiments of the first-fourth embodiments, applying of liquid binder comprises a combination of selective application of liquid binder to less than the entire rubber layer of certain rubber layer(s) and application of liquid binder to the entire rubber layer of other rubber layer(s). In certain embodiments of the first-fourth embodiments, each step of applying actinic radiation comprises application of the actinic radiation to the entire surface of the bound layer; in certain such embodiments, this includes application of the actinic radiation to the entire surface of each bound layer and in other embodiments this includes application of the actinic radiation to the entire surface of less than each bound layer. In certain embodiments of the first-fourth embodiments, some of the steps of applying actinic radiation comprise application of the actinic radiation to the entire surface of the bound layer and other steps of applying actinic radiation comprise application of the actinic radiation to the entire surface of the bound layer.

According to the first-fourth embodiments, the applying of actinic radiation, heat, or a combination thereof to the first bound layer and/or to the additional bound layers may take place for varying amounts of time, depending generally upon the type and intensity of radiation or heat applied as well as the thickness of the bound layer(s) and the ingredients contained within the bound layer (i.e., liquid binder and rubber particles). According to certain embodiments of the first-fourth embodiments, each application of actinic radiation, heat, or a combination thereof may take place for the same amount of time or for a different amount of time (e.g., for each respective bound layer to which the actinic radiation, heat, or a combination thereof is applied). According to certain embodiments of the first-fourth embodiments, the applying of actinic radiation to the first bound layer and/or to the additional bound layers takes place for about 0.1 to about 60 seconds (e.g., 0.1, 0.5, 1, 5, 10, 15, 20, 30, 40, 45, 50, or 60 seconds). According to certain embodiments of the first-fourth embodiments, the applying of heat to the first bound layer and/or to the additional bound layers takes place for about 60 to about 900 seconds (e.g., 60, 120, 180, 240, 300, 360, 420, 480, 540, 600, 660, 720, 780, 840, or 900 second); in certain such embodiments the bound layer(s) are heated to a temperature of about 100 to about 250° C. (e.g., 100, 101, 102, 103, 104, 105, 110, 120, 130, 140, 150, 160, 170, 180, 190, 200, 210, 220, 230, 240, 250° C.).

Second Curing

In certain embodiments of the first-fourth embodiments, a second curing step is applied after the first curing (within the additive manufacture device) is complete. As explained above, the initial curing which takes place (generally while the product is within the additive manufacturing device) by applying actinic radiation, heat, or a combination thereof may result in a polymeric product which does not have the desired mechanical properties for its intended use. In such embodiments, a second curing may be effected in order to produce a cured polymeric product which has improved mechanical properties. In certain embodiments of the first-fourth embodiments, the second curing takes place outside of the additive manufacturing device. In such embodiments, the second curing may be affected at various times after the first curing is complete, e.g., minutes (e.g., 1-59 minutes) after the first curing is complete, hours (e.g., 1-23.9 hours) after the first curing is complete, days (e.g., 1-6.9 days) after the first curing is complete, or even weeks (e.g., 1-12 weeks, 1-8 weeks, 1-4 weeks) after the first curing is complete. In certain embodiments of the first-fourth embodiments, the second curing utilizes heat, actinic radiation (preferably IR), or a combination thereof. In certain embodiments of the first-fourth embodiments, a second curing is utilized, optionally outside of the additive manufacturing device, wherein the second curing utilizes heat, actinic radiation (preferably IR), or a combination thereof.

When a second curing is utilized, the particular conditions used to achieve that second curing may vary. Based upon the composition (ingredients) and size of the particular cured polymeric product, one of skill in the art can determine appropriate conditions for the second curing. Generally, if heat is utilized to effect the second curing, the temperature may vary from about 100 to about 250° C. (e.g., 100, 101, 102, 103, 104, 105, 110, 120, 130, 140, 150, 160, 170, 180, 190, 200, 210, 220, 230, 240, 250° C.), or about 110 to about 200° C. (with the foregoing temperatures referring to temperature of the environment).

Mechanical Properties

In certain embodiments of the first-fourth embodiments, the cured polymeric product has specific mechanical properties which can be measured upon a sample of the material used to make the cured polymeric product. In certain embodiments of the first-fourth embodiments, the cured polymeric product has a tensile at break (Tb) of 1 MPa to 35 MPa (e.g., 1 MPa, 5 MPa, 10 MPa, 15 MPa, 20 MPa, 25 MPa, 30 MPa, or 35 MPa), or 5 MPa to 25 MPa. As discussed in more detail below, tensile at break provides a measure of a composition's strength in terms of the maximum amount of force which can be applied before a breakage occurs. In certain embodiments of the first-fourth embodiments, the cured polymeric product has a tensile strength at 300% elongation of 1 MPa to 12 MPa (e.g., 1 MPa, 2 MPa, 3 MPa, 4 MPa, 5 MPa, 6 MPa, 7 MPa, 8 MPa, 9 MPa, 10 MPa, 11 MPa, or 12 MPa), or 4 MPa to 8 MPa. As discussed in more detail below, tensile strength at 300% elongation provides another measure of a composition's strength by measuring the maximum amount of force which can be applied before an elongated sample breaks. In certain embodiments of the first-fourth embodiments, the cured polymeric product has an elongation at break (Eb) of 50% to 800% (e.g., 50%, 100%, 150%, 200%, 250%, 300%, 350%, 400%, 450%, 500%, 550%, 600%, 650%, 700%, 750%, 800%), or 100% to 600%. As discussed in more detail below, elongation at break provides a measure of a composition's ability to stretch without breaking by measuring the percentage of elongation which can be applied before a sample breaks. In certain embodiments of the first-fourth embodiments, the cured polymeric product has a shear modulus of 0.5 dNm to 50 dNm (e.g., 0.5, 1, 2, 3, 4, 5, 7, 10, 15, 20, 25, 30, 35, 40, 45, 50 dNm), or 1 dNm to 25 dNm). As discussed in more detail below, shear modulus (G') provides a measure of a composition's stiffness or viscosity. In certain embodiments of the first-fourth embodiments, the cured polymeric product has at least one of the foregoing mechanical properties (i.e., tensile at break, tensile strength at 300%, elongation at break, or shear modulus). In other embodiments of the first-fourth embodiments, the cured polymeric product has tensile at break, tensile strength at 300%, elongation at break, and shear modulus properties which each fall within one of the foregoing ranges. In certain embodiments of the first-fourth embodiments, the cured polymeric product has at least one of the following mechanical properties: (a) tensile at break (Tb) of 1 MPa to 35 MPa, preferably 5 MPa to 25 MPa; (b) tensile strength at 300% elongation of 1 MPa to 12 MPa, preferably 4 MPa to 8 MPa; (c) elongation at break (Eb) of 50% to 80%, preferably 100% to 600%; or (d) shear modulus of 0.5 dNm to 50 dNm, preferably 1 dNm to 25 dNm. In certain embodiments of the first-fourth embodiments, the cured polymeric product meets each of (a)-(d) mechanical properties.

The foregoing mechanical properties of the samples can be determined following the guidelines of, but not restricted to, the standard procedure described in ASTM D-412, using dumbbell-shaped samples with a cross-section dimension of 4 mm in width and 1.9 mm in thickness at the center, cured for 15 minutes at 170° C. The dumbbell-shaped sample used for mechanical testing can be made using the same materials in the same relative amounts (e.g., rubber particles, liquid binder etc.) as the polymeric article, same process for forming the layers (e.g., thickness of rubber layers) and the cure conditions as described above. Specimens should be strained at a constant rate and the resulting force recorded as a function of extension (strain). Force readings for shear modulus can be reported as engineering-stresses by reference to the original cross-sectional area of the test piece. The specimens are tested at 25° C. unless indicated to the contrary.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, *A Dictionary of Modern Legal Usage* 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the application, in its broader aspects, is not limited to the specific details and embodiments described. Accordingly, departures may be made from such details without departing from the spirit or scope of the applicant's general inventive concept.

This application discloses several numerical range limitations that support any range within the disclosed numerical ranges even though a precise range limitation is not stated verbatim in the specification because the embodiments could be practiced throughout the disclosed numerical ranges. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As well, all numerical limitations and ranges that are preceded by the word "about" should be understood to include the particular number or range without the about as if fully set forth herein.

What is claimed is:

1. A process for producing a cured polymeric product by additive manufacturing, comprising:

providing an additive manufacturing device comprising a source of actinic radiation, a tank capable of containing a binder, and a support structure;

forming rubber particles into a first rubber layer upon the support structure, wherein the rubber particles comprise at least one conjugated diene-monomer containing polymer and reinforcing filler, wherein the rubber particles are in paste form, comprise uncured rubber, or are in paste form and comprise uncured rubber;

applying liquid binder to the first rubber layer to form a first bound layer, wherein the liquid binder comprises a curable polymeric mixture and optionally a cure package;

sequentially forming additional rubber layers upon the first bound layer and applying liquid binder to at least some of the additional rubber layers to form additional bound layers; and effecting curing by applying actinic radiation, heat, or a combination thereof to one or more of the bound layers, thereby producing a cured polymeric product.

2. The process of claim 1, wherein the rubber particles have an average particle size of about 10 microns to about 1000 microns.

3. The process of claim 1, wherein the at least one conjugated diene monomer-containing polymer of the rubber particles comprises uncured rubber.

4. The process of claim 1, wherein the at least one conjugated diene monomer-containing polymer of the rubber particles comprises cured rubber.

5. The process of claim 1, wherein the rubber particles are in powder form.

6. The process of claim 1, wherein the rubber particles are in paste form.

7. The process of claim 1, wherein the curable polymeric mixture of the liquid binder further comprises at least one of: UV curable resin, IR curable resin, heat curable resin, thermoset polymer, thermoplastic polymer, or thermoplastic elastomer.

8. The process of claim 1, wherein the weight ratio of rubber particles to liquid binder in the first layer and any additional layers is 25/75 to 99/1.

9. The process of claim 1, wherein the curable polymeric mixture of the liquid binder comprises an actinic radiation curable polymeric mixture.

10. The process of claim 9, wherein the actinic radiation curable polymeric mixture comprises:
   (a) a polyfunctionalized diene monomer-containing polymer having the formula:
      [P][F]$_n$ wherein P represents a diene monomer-containing polymer chain, F represents a functional group, n is 2 to about 15, and each F can be the same or different;
   (b) optionally a chain extender based upon F or reactive with F;
   (c) at least one actinic radiation sensitive photoinitiator;
   (d) optionally a photosensitizer; and
   (e) a polyfunctional crosslinker reactive with F.

11. The process of claim 10, wherein the total amount of (a) and (b) is 100 parts and (c) is present in a total amount of at least about 0.1 parts (based upon 100 parts of (a) and (b)), and at least one of the following is met:
   (i) the polyfunctionalized diene monomer-containing polymer (a) is present in an amount of 1-100 parts and (b) is present in an amount of 0-99 parts;
   (ii) the photosensitizer (d) is present in an amount of about 0.1 parts to about 5 parts (per 100 total parts of (a) and (b));

(iii) each F comprises at least one of: acrylate, methacrylate, cyanoacrylate, epoxide, aziridine, or thioepoxide;
(iv) F comprises a free radical polymerizable functional group;
(v) F comprises a cationic polymerizable functional group;
(vi) the polyfunctionalized diene monomer-containing polymer (a) comprises a combination of cationic polymerizable and free radical polymerizable groups either on the same diene polymer chain or on separate diene polymer chains;
(vii) the polyfunctionalized diene monomer-containing polymer (a) has a Mn of about 3,000 to about 135,000 grams/mole (polystyrene standard);
(viii) the diene monomer-containing polymer chain comprises monomers selected from at least one of acyclic and cyclic dienes having 3 to about 15 carbon atoms;
(ix) the Tg of the polyfunctionalized diene monomer-containing polymer is about—105 to about −10 C;
(x) the diene monomer-containing polymer chain comprises monomers selected from at least one of: 1,3-butadiene, isoprene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, 2,4-hexadiene, 1,3-cyclopentadiene, 1,3-cyclohexadiene, 1,3-cycloheptadiene, 1,3-cyclooctadiene, farnescene, and substituted derivatives of each of the foregoing; or
(xi) in addition to (viii) above, the diene polymer chain further comprises at least one vinyl aromatic monomer.

12. The process of claim 1, wherein applying of actinic radiation comprises selective application of actinic radiation to less than the entire layer of at least some of the bound layers.

13. The process of claim 1, wherein the reinforcing filler of the rubber particles comprises carbon black in an amount of about 20 to about 40% by weight of the rubber particles, and the rubber particles further comprise at least one of: oil, stearic acid, sulfur, or zinc oxide.

14. The process of claim 1, wherein each bound layer has a thickness of about 10 to about 1000 microns.

15. The process of claim 1, further comprising:
effecting a second curing, optionally outside of the additive manufacturing device, wherein the second curing utilizes heat, actinic radiation, or a combination thereof.

16. The process of claim 1, wherein the cured polymeric product has at least one of the following mechanical properties:
a. tensile at break (Tb) of 1 MPa to 35 MPa;
b. tensile strength at 300% elongation of 1 MPa to 12 MPa;
c. elongation at break (Eb) of 50% to 800%; or d. shear modulus of 0.5 dNm to 50 dNm.

17. A cured polymeric product produced according to the process of claim 1.

18. A process for producing a cured tire component polymeric product by additive manufacturing, comprising:
providing an additive manufacturing device comprising a source of actinic radiation, a tank capable of containing a binder, and a support structure;
forming rubber particles into a first rubber layer upon the support structure, wherein the rubber particles comprise at least one conjugated diene-monomer containing polymer and reinforcing filler, wherein the rubber particles are in paste form, comprise uncured rubber, or are in paste form and comprise uncured rubber;
applying liquid binder to the first rubber layer to form a first bound layer, wherein the liquid binder comprises a curable polymeric mixture and optionally a cure package;
sequentially forming additional rubber layers upon the first bound layer and applying liquid binder to at least some of the additional rubber layers to form additional bound layers; and
effecting curing by applying actinic radiation, heat, or a combination thereof to one or more of the bound layers, thereby producing a cured polymeric product.

19. The process of claim 18, wherein the curable polymeric mixture of the liquid binder comprises an actinic radiation curable polymeric mixture comprising:
(a) a polyfunctionalized diene monomer-containing polymer having the formula:
[P][F]$_n$ wherein P represents a diene monomer-containing polymer chain, F represents a functional group, n is 2 to about 15, and each F can be the same or different;
(b) optionally a chain extender based upon F or reactive with F;
(c) at least one actinic radiation sensitive photoinitiator;
(d) optionally a photosensitizer; and
(e) a polyfunctional crosslinker reactive with F.

20. The process of claim 19, wherein the cured tire component polymeric product has the following mechanical properties:
a. tensile at break (Tb) of 5 MPa to 35 MPa;
b. tensile strength at 300% elongation of 4 MPa to 12 MPa;
c. elongation at break (Eb) of 100% to 600%; and
d. shear modulus of 1 dNm to 25 dNm.

21. The cured polymeric product of claim 17 in the form of an air spring.

22. The process of claim 18, wherein the at least one conjugated diene monomer-containing polymer of the rubber particles comprises cured rubber.

23. The process of claim 18, wherein the rubber particles are in powder form.

24. The process of claim 18, wherein the rubber particles are in paste form.

* * * * *